US010575933B2

(12) United States Patent
Berg et al.

(10) Patent No.: US 10,575,933 B2
(45) Date of Patent: Mar. 3, 2020

(54) CASSETTE FOR STORAGE OF MEDICAL INSTRUMENTS

(71) Applicant: STRAUMANN HOLDING AG, Basel (CH)

(72) Inventors: Marianne Berg, Zürich (CH); Friedhelm Kraft, Heuchelheim (DE); Silvio Blumenthal, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 241 days.

(21) Appl. No.: 15/557,416

(22) PCT Filed: Mar. 7, 2016

(86) PCT No.: PCT/EP2016/054767
§ 371 (c)(1),
(2) Date: Sep. 11, 2017

(87) PCT Pub. No.: WO2016/142331
PCT Pub. Date: Sep. 15, 2016

(65) Prior Publication Data
US 2018/0271632 A1    Sep. 27, 2018

(30) Foreign Application Priority Data

Mar. 9, 2015    (EP) .................................... 15158228

(51) Int. Cl.
*A61C 19/02*    (2006.01)
*A61C 3/04*    (2006.01)
(Continued)

(52) U.S. Cl.
CPC .............. *A61C 19/02* (2013.01); *A61B 50/20* (2016.02); *A61B 50/30* (2016.02); *A61B 50/33* (2016.02);
(Continued)

(58) Field of Classification Search
CPC ........... A61C 19/02; A61C 3/04; A61B 50/20; A61B 50/30; A61B 50/33; A61B 50/34
(Continued)

(56) References Cited

U.S. PATENT DOCUMENTS 1,451,806 A * 4/1923 Baldridge ................ A61C 3/04
206/369
4,135,868 A * 1/1979 Schainholz ............... A61L 2/26
206/438
(Continued)

FOREIGN PATENT DOCUMENTS

EP    2 163 219 B1    4/2012
FR    2 898 278 A1    9/2007
(Continued)

OTHER PUBLICATIONS

May 10, 2016 International Search Report issued in International Patent Application No. PCT/EP2016/054767.
(Continued)

*Primary Examiner* — Chun Hoi Cheung
(74) *Attorney, Agent, or Firm* — Oliff PLC

(57) ABSTRACT

A cassette for storage of at least one medical instrument, the cassette including at least one spring sheet, the spring sheet including at least one holding means for retaining the medical instrument therein, the holding means including an aperture forming a passage through the spring sheet for receiving the medical instrument and at least one spring element provided adjacent to the passage for exerting a biasing spring force to retain the medical instrument within the passage, and wherein the spring sheet, including the holding means, is made of a metal or a metal alloy.

21 Claims, 15 Drawing Sheets

(51) Int. Cl.
*A61B 50/33* (2016.01)
*A61B 50/34* (2016.01)
*A61B 50/20* (2016.01)
*A61B 50/30* (2016.01)
*A61L 2/26* (2006.01)

(52) U.S. Cl.
CPC ............... *A61B 50/34* (2016.02); *A61C 3/04* (2013.01); *A61L 2/26* (2013.01); *A61L 2202/182* (2013.01)

(58) Field of Classification Search
USPC .................................. 206/369, 370, 380, 379
See application file for complete search history.

(56) References Cited

U.S. PATENT DOCUMENTS

| | | | | |
|---|---|---|---|---|
| 4,541,992 A * | 9/1985 | Jerge | A61C 19/02 | 422/300 |
| 4,643,303 A * | 2/1987 | Arp | A61L 2/26 | 206/370 |
| 4,798,292 A * | 1/1989 | Hauze | A61L 2/26 | 206/439 |
| 4,959,199 A * | 9/1990 | Brewer | A61C 19/00 | 206/439 |
| 5,071,346 A * | 12/1991 | Domaas | A61C 3/04 | 206/369 |
| 5,084,251 A * | 1/1992 | Thomas | A61C 19/02 | 206/557 |
| 5,174,453 A * | 12/1992 | Stoeffler | A61L 2/26 | 206/370 |
| 5,215,726 A * | 6/1993 | Kudla | A61L 2/26 | 422/297 |
| 5,284,632 A * | 2/1994 | Kudla | A61L 2/26 | 422/297 |
| 5,294,413 A * | 3/1994 | Riihimaki | A61L 2/26 | 206/263 |
| 5,346,677 A * | 9/1994 | Risk | A61C 19/02 | 206/363 |
| 5,384,103 A | 1/1995 | Miller | | |
| 5,505,916 A * | 4/1996 | Berry, Jr. | A61L 2/06 | 422/300 |
| 5,525,314 A * | 6/1996 | Hurson | A61C 3/04 | 206/369 |
| 5,681,539 A * | 10/1997 | Riley | A61L 2/26 | 206/370 |
| 5,732,821 A * | 3/1998 | Stone | A61L 2/26 | 206/370 |
| 5,759,502 A * | 6/1998 | Spencer | A61L 2/26 | 206/370 |
| 5,827,487 A * | 10/1998 | Holmes | A61L 2/26 | 422/297 |
| 5,829,590 A * | 11/1998 | Klein | A61C 3/04 | 206/369 |
| 5,913,422 A * | 6/1999 | Cote | A61L 2/26 | 206/210 |
| 5,979,643 A | 11/1999 | Blonder et al. | | |
| 6,436,357 B1 * | 8/2002 | Frieze | A61L 2/26 | 206/263 |
| 6,969,498 B1 * | 11/2005 | Riley | A61L 2/26 | 206/363 |
| 7,066,329 B2 * | 6/2006 | Riley | A61C 3/04 | 206/369 |
| 7,341,148 B2 * | 3/2008 | Bettenhausen | A61L 2/18 | 206/370 |
| 7,544,336 B2 * | 6/2009 | Powell | A61L 2/26 | 206/363 |
| 8,069,998 B2 * | 12/2011 | Thomas | A61L 2/26 | 211/85.13 |
| 8,272,508 B2 * | 9/2012 | Bettenhausen | A61L 2/26 | 206/370 |
| 8,827,088 B1 * | 9/2014 | Krause | A61L 9/00 | 211/85.13 |
| 8,887,913 B2 * | 11/2014 | Wood | A61C 3/04 | 206/338 |
| 8,936,151 B2 * | 1/2015 | Abene | A61C 19/02 | 206/369 |
| 9,198,811 B2 * | 12/2015 | Pizzato | A61F 17/00 | |
| 9,636,429 B2 * | 5/2017 | Cushion | A61L 2/00 | |
| 10,278,790 B2 * | 5/2019 | Zieris | A61B 50/30 | |
| 2003/0196922 A1 | 10/2003 | Reaux | | |
| 2004/0074795 A1 * | 4/2004 | Fischer | A61C 19/02 | 206/366 |
| 2005/0035015 A1 | 2/2005 | Bressler et al. | | |
| 2005/0161355 A1 * | 7/2005 | Matthis | A61C 19/02 | 206/370 |
| 2005/0249651 A1 * | 11/2005 | Riley | A61L 2/26 | 422/300 |
| 2007/0104609 A1 * | 5/2007 | Powell | A61L 2/26 | 422/1 |
| 2007/0119737 A1 * | 5/2007 | Wood | A61B 50/22 | 206/363 |
| 2007/0205123 A1 * | 9/2007 | Bettenhausen | A61B 50/34 | 206/363 |
| 2011/0071572 A1 * | 3/2011 | Sixto | A61B 17/8014 | 606/286 |
| 2011/0139651 A1 * | 6/2011 | Fujii | A61C 3/04 | 206/369 |
| 2012/0094249 A1 * | 4/2012 | Abene | A61C 3/04 | 433/77 |
| 2012/0138495 A1 * | 6/2012 | Bettenhausen | A61L 2/26 | 206/339 |
| 2013/0046289 A1 * | 2/2013 | Allen | A61L 2/26 | 606/1 |
| 2013/0061445 A1 * | 3/2013 | Allen | A61B 50/20 | 29/428 |
| 2013/0064709 A1 * | 3/2013 | Allen | A61L 2/26 | 422/1 |
| 2013/0334083 A1 * | 12/2013 | Bugnard | A61C 19/02 | 206/370 |
| 2014/0014544 A1 * | 1/2014 | Bugnard | A61C 19/02 | 206/369 |
| 2014/0069841 A1 * | 3/2014 | Pizzato | A61F 17/00 | 206/570 |
| 2014/0170592 A1 * | 6/2014 | Johansson | A61C 3/04 | 433/77 |
| 2014/0202903 A1 * | 7/2014 | Dassonville | A61C 3/04 | 206/370 |
| 2017/0143449 A1 * | 5/2017 | Zieris | A61B 50/30 | |

FOREIGN PATENT DOCUMENTS

| | | |
|---|---|---|
| WO | 2005/053597 A2 | 6/2005 |
| WO | 2006/071180 A1 | 7/2006 |
| WO | 2007/056399 A1 | 5/2007 |
| WO | 2012/084199 A1 | 6/2012 |

OTHER PUBLICATIONS

May 10, 2016 Written Opinion of the International Searching Authority issued in International Patent Application No. PCT/EP2016/054767.

* cited by examiner

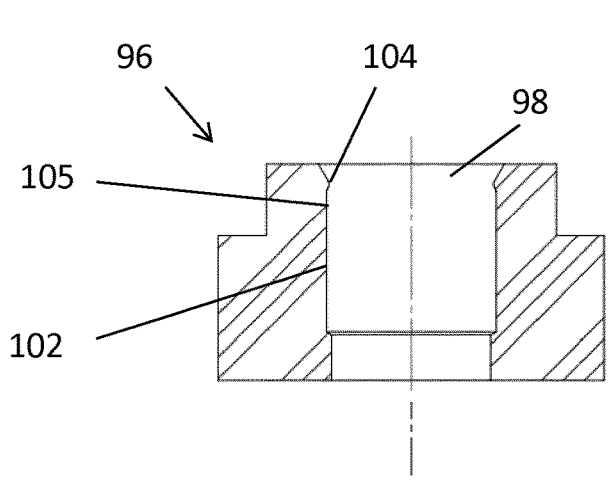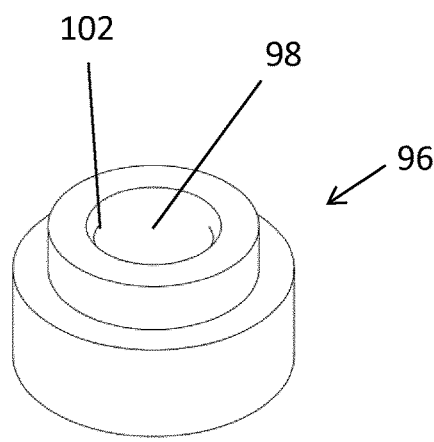
Fig. 8A     Fig. 8B
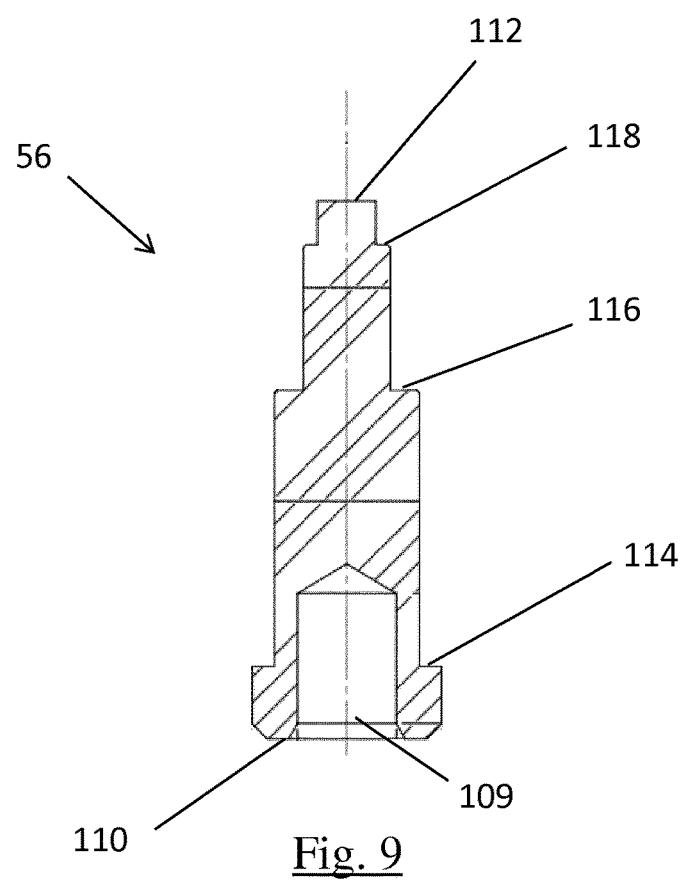
Fig. 9

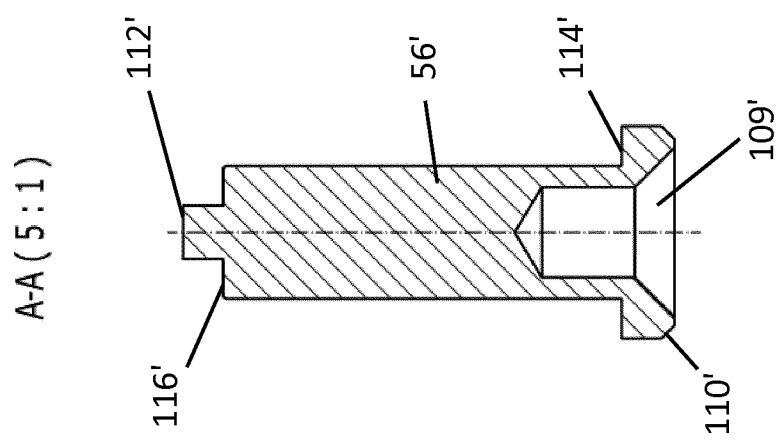
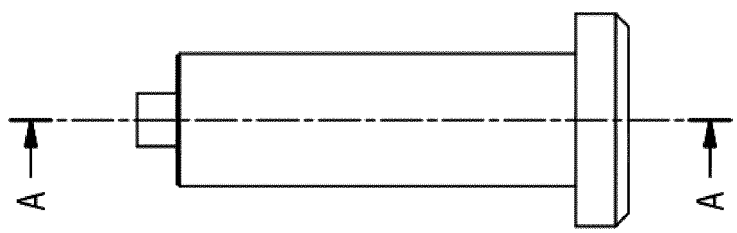
Fig. 21

CASSETTE FOR STORAGE OF MEDICAL INSTRUMENTS

The invention relates to a cassette for storage, cleaning and sterilization of at least one medical instrument, in particular a dental surgical tool.

Cassettes for storage, organization and presentation of medical instruments represent well-known systems in the art. Most of these cassettes comprise at least one tray with holding means in which the medical instruments are accommodated and a cover to close the tray.

Such a cassette is disclosed for instance in U.S. Pat. No. 5,525,314. The surgical tool container described therein comprises an outer case having a separable lid and base portion and a tool-holding tray removably inserted within the base portion. Elastomeric grommets and resilient finger brackets are secured on the tool-holding tray for accommodating shanks of the surgical tools, such that the latter are removably held by these elastic elements due to frictional engagement therewith.

A further cassette including an instrument tray and a cover for storage, transport and sterilization of medical instruments is disclosed in U.S. Pat. No. 5,384,103. Interchangeably disposed along the surface of the tray and cover are a plurality of support members, whereby each support member includes variously dimensioned, notched receptacles for receiving a respective medical instrument. The support members are made of resilient material which is capable of replaceably accommodating medical instruments.

Further examples of cassettes for storage of medical instruments are described, e.g. in EP 2163219, U.S. Pat. No. 5,979,643, WO 2005/053597, WO 2006/071180 and US 2007/0119737.

In the cassettes of the prior art, the holding means usually comprise elastomeric material and are usually fixed on the tray, e.g. by form fit, molding, welding or gluing. Although such elastomeric materials provide a good hold on the medical instruments, these materials can also have severe disadvantages.

One problem is that these materials are sensitive and prone to environmental pollution. For instance, they can easily get contaminated with blood or soft tissue when the instruments are grabbed by the surgeon with contaminated surgical gloves.

Rising hygiene standards require the instruments to be cleaned and sterilized within the cassette. Thus, the instruments and the cassette should not be cleaned separately any more but in the assembled state by Automated Cleaning and Disinfection (ACD) machines. However, problems arise if elastomeric components are included in the cassettes. Firstly, the method of connection between the elastomeric holding means and cassette often results in undercuts and other small spaces in which dirt can collect and which are difficult to clean. Additionally the cleaning agents used in the ACD machines can affect the properties of the elastomeric material, e.g. by removing the softener. This affects the ability of the holding means to reliably grip the instrument and increases the adhesion of dirt particles to the holding means. Further, when a cassette comprises two or more different types of material these will have different heating and cooling rates, as well as different rates of thermal expansion. This can lead to stresses within the cassette as well as condensation problems. As the cassette should be completely free of water prior to sterilisation, condensation formation on the holding means can be problematic.

Therefore, the problem to be solved by the present invention is to provide a cassette for one or a plurality of medical instruments which allows safe holding, storing, cleaning and sterilization of the medical instrument(s) within and which can be cleaned in an ACD machine without damage to the cassette.

According to one aspect therefore the present invention provides a cassette for storage of at least one medical instrument, the cassette comprising at least one spring sheet, the spring sheet comprising at least one holding means for retaining the medical instrument therein, the holding means comprising an aperture forming a passage through the spring sheet for receiving the medical instrument and at least one spring element provided adjacent to the passage for exerting a biasing spring force to retain the medical instrument within the passage, and wherein the spring sheet, including the holding means, is made of a metal or a metal alloy.

The term "sheet" as used in the context of the present invention relates to a, preferably planar, structure whose thickness is smaller than its length and width and by the term "a passage" therethrough it is meant that the passage extends through the thickness of the spring sheet.

Thus, the present invention provides a holding means which can be formed entirely of metal or metal alloy and hence prevents the problems associated with the use of elastomeric grommets. This is achieved by removably holding the at least one medical instrument, such as a drill, insertion tool, wrench, punch, tap etc., within a passage in the spring sheet by means of at least one spring element positioned adjacent to the passage and configured to releasably retain the medical instrument therein. The retentive force is thus provided by a metal or metal alloy component and not an elastomeric material.

In order to retain the medical instrument within the holding means, the cross-section of the passage is restricted by the at least one adjacent spring element to an extent that the medical instrument can only be inserted into the holding means under deformation of the spring element(s). Thus, in general, the cross-section or diameter of the passage, which is in part defined by the adjacent spring element(s), is at least slightly smaller than the diameter of the medical instrument when the at least one spring element is in its resting position. It goes without saying that by the "instrument diameter" and "instrument cross-section" it is hereby referred to the cross-section and the diameter of that part of the instrument which is to be accommodated within the holding means.

When inserting the medical instrument into the holding means, the outer surface of the medical instrument comes into contact with the at least one spring element, whereupon the spring element is compressed and/or deflected in a direction in the plane of the spring sheet. This compression and/or deflection of the spring element (and the fact that the spring element aims to return to its resting position) results in the generation of a biasing spring force, by means of which the medical instrument is retained within the passage. Thus, the provision of the at least one spring element enables a releasable retention of the medical instrument within the holding means of the spring sheet by creating a friction fit connection. The retentive force of the friction connection is preferably limited to a degree which allows a relatively easy retrieval of the medical instrument from the holding means, e.g. by simply pulling the medical instrument along its longitudinal axis out of the holding means. Nevertheless, the retentive force allows the holding means to safely hold the medical instrument within the spring sheet during the course of various events such as cleaning, sterilisation, packing, transportation and storage, such that accidental dislocation of the medical instrument is prevented.

The cassette of the present invention therefore enables organization, protection and thorough cleaning and sterilization of at least one medical instrument stored within the cassette. The spring sheet allows for holding the medical instrument in a secure manner, yet also permits the instrument to be readily removed from the cassette for use.

The cross-section of the passage, in the plane of the spring sheet, can be any shape suitable for housing a particular medical instrument, e.g. circular, oval, polygonal etc.

Preferably the cross-section of the passage comprises two or more areas of contact surface for contacting the medical instrument, one of said contact surfaces being formed by a surface of the at least one spring element and said contact surfaces being spaced apart from one another about the circumference of the passage. This results in areas of non-contact being formed around the cross-section of the passage. These areas create channels that allow a flow of cleaning fluid through the passage even when a medical instrument is held therein. The areas of contact between the holding means and medical instrument should be kept to a minimum while at the same time ensuring adequate support to the instrument. Preferably the cross-section of the passage is provided with three areas of contact surface interposed by recesses. In one embodiment the areas of contact surface are concave arcs for contacting a circular cylindrical shaft of a medical instrument, and the recesses are formed by indents located between these arcs. In an alternative embodiment the areas of contact can be provided by convex nubs that protrude into the passage.

The diameter of the passage through the spring sheet can remain constant, decrease or increase at various stages along its length. This means that it is also possible for the diameter of the passage to undergo a step change. Preferably however the diameter and cross-section of the passage remains constant along its length.

The at least one spring element of the holding means can be a separate component which is inserted, clamped, welded or otherwise attached to the spring sheet. For example, the spring element may be inserted in to a groove or cavity within or beside the aperture and held in place by a positive (form) or non-positive (friction) fit.

Preferably however, the at least one spring element is integrally formed in one piece with the spring sheet. In this way, there is no join between the spring element and the spring sheet into which bacteria, fluids, dirt etc. could enter, which allows a better cleaning. In addition, the provision of an integrally formed spring element in the spring sheet facilitates the production of the latter and greatly increases the stability of the spring element itself. As a result, the production costs of the spring sheet can be lowered and the overall lifetime increased.

In such embodiments the at least one spring element and the spring sheet form a monolithic structure. A spring element that is integrally formed in one piece with the spring sheet can be prepared for instance by cutting the spring sheet, preferably by means of a water stream or laser cutting procedure, or by injection moulding or machining. When the at least one spring element is integrally formed with the spring sheet in most instances the spring element will extend the length of the passage, or in other words the thickness of the spring sheet, and hence will supply a biasing force to the instrument along the length of the passage.

The at least one spring element can have any shape which enables it to be deflected and/or compressed in the plane of the spring sheet such that it exerts a biasing force into the adjacent passage. In some embodiments the spring element may also in addition be compressed and/or deflected in a direction perpendicular to the plane of the spring sheet.

In a preferred embodiment the at least one spring element comprises a tongue having an attachment end connected to the spring sheet, preferably integrally formed therewith in one piece, and a free end arranged at the opposing end of the tongue, the tongue having a contact surface, preferably in the area of the free end, which is designed to abut against the medical instrument for retaining the latter within the passage.

The contact surface of the tongue may be centred about the central longitudinal axis of the tongue. In such embodiments the tongue will usually extend non-linearly along said axis, e.g. the tongue may have a "zig-zag" or "kinked" shape. However, the location of the contact surface of the tongue is preferably such that its normal axis, i.e. the axis running perpendicular to the plane of the contact surface, is oriented at an angle to the longitudinal axis of the tongue, preferably at an angle of 45° to 135°, more preferably at an angle of approximately 90°. When the medical instrument is inserted into the passage and brought into contact with the contact surface, this angle enables the spring element to be deflected in the plane of the spring sheet relative to the attachment end, thus creating the biasing force.

When the medical instrument is inserted into the passage, the contact surface of the tongue engages with the outer surface of the instrument and the tongue is thereby deflected from its resting position laterally in the plane of the spring sheet, such that the diameter of the passage is widened to allow insertion of the instrument. The biasing force applied by the contact surface to the instrument as the spring element attempts to return to its resting position retains the instrument within the holding means.

The spring characteristics, in particular the bending properties of the tongue can be adjusted by altering the length, width and/or the thickness of the tongue. In addition, the tongue can be provided with one or more slots which allow for an increased bending capacity of the tongue.

According to an alternative preferred embodiment, the at least one spring element is formed by a spring bridge having at either end an attachment end attached to the spring sheet, preferably integrally formed therewith in one piece, such that the spring bridge protrudes into the passage. In this way the spring bridge forms a "C" or "⊃" shape. In this embodiment, the contact surface is provided on the outer surface of the spring bridge. Thus, upon insertion of the medical instrument into the passage, the contact surface abuts against the outer surface of the medical instrument and the spring bridge is thereby compressed and/or deflected radially away from the longitudinal axis of the medical instrument in the direction of the plane of the spring sheet.

It is possible for the holding means of the present invention to comprise a plurality of spring elements. For example, the holding means could comprise two spring elements on opposing sides of the passage. Upon insertion of a medical tool into the passage the spring elements would be deflected and/or compressed in opposite directions and each would then supply a biasing force to the instrument which presses it towards the contact surface of the opposing spring element. In this way the medical instrument would be retained between the spring elements.

Preferably however the at least one holding means of the present invention comprises a single spring element. This simplifies the design and manufacture of the spring sheet. In such embodiments the single spring element of the holding means exerts a biasing spring force to press the medical instrument against the interior wall of the passage. Therefore at least one area of contact surface is formed on the interior wall of the passage, preferably at least two areas circumferentially spaced from each other in order to allow fluid to pass through the passage when an instrument is retained therein. Thus, the effective diameter of the passage is limited by the contact surfaces on the interior wall of the passage and on the spring element, which can be elastically pushed back to provide sufficient space for the medical instrument to fit within the passage.

In one embodiment the aperture of the at least one holding means is open to a lateral edge of the spring sheet, thereby forming a laterally open passage for allowing insertion of the medical instrument. In this preferred embodiment it is preferable that the spring sheet is positioned vertically within the cassette. That is to say, the spring sheet extends substantially perpendicular to the horizontal plane of the cassette.

According to an alternative preferred embodiment the aperture of the at least one holding means has a closed cross-section such that the medical instrument is inserted into the aperture along an axis coaxial to the passage. In this preferred embodiment it is preferable that the spring sheet is oriented essentially parallel to the horizontal plane of the cassette such that the passage extends through the sheet from the upper to lower surface.

All references to horizontal and vertical orientations refer to the orientation of the components when the cassette is positioned on a flat surface in its correct orientation, i.e. with its lower surface facing the flat surface.

Preferably the cassette comprises a base tray and a cover part forming an outer housing, the at least one spring sheet being located within said outer housing. Preferably said base tray and cover part are made of metal or metal alloy. This prevents the aforementioned problems that can arise when the cassette comprises materials having different heating and cooling rates.

In such preferred embodiments, when the aperture of the holding means is open to a lateral edge of the spring sheet, it is preferable that one edge of the spring sheet is fixed to the base tray such that it protrudes therefrom in a direction substantially perpendicular to the base tray and thus is positioned vertically within the cassette. In this embodiment it is particularly preferred that the aperture is open to a top edge of the spring sheet, namely that edge facing away from the base tray, such that the medical instrument can be inserted laterally into the aperture, whereby the longitudinal axis of the instrument is oriented more or less perpendicular to the plane of the spring sheet and parallel to the plane of the base tray.

In this embodiment it is further preferred that the at least one holding means in the spring sheet is provided with a shape which can provide the user with physical feedback once the medical instrument is securely fastened within the holding means. Such a physical feedback can be achieved, for instance, by providing a protruding detent or nub on the interior wall of the passage, past which nub the maximum diameter of the instrument must be pushed in order to correctly seat the instrument within the passage. In this way, the medical instrument can be laterally pressed into the aperture and as the maximum diameter of the medical instrument overcomes the nub, the user is provided with a physical sensation, e.g. a jolt, snap or reduction in resistance, that informs them that the medical instrument is correctly seated and is latched into the aperture under deformation of the spring element.

In a further embodiment, when the aperture of the holding means is open to a lateral edge of the spring sheet, the cassette further comprises at least one secondary sheet, whereby the spring sheet and secondary sheet are fixed to the base tray such that they protrude therefrom in a direction substantially perpendicular to the base tray and are spaced apart by a certain distance. Preferably, the spring sheet and secondary sheet protrude vertically from the base tray and are either arranged essentially parallel or at a predefined angle to each other. The secondary sheet comprises at least one aperture open to a lateral edge of the sheet within which the medical instrument can be received. The size and shape of the aperture can be adjusted in accordance with the size and shape of the medical instrument to be received therein. The use of one or more secondary sheets ensures that the medical instrument is supported along its length and prevents the instrument from tilting along its longitudinal axis, which could result in it detaching from the holding means or interfering with other instruments housed within the cassette. The medical instrument is retained by the holding means in the spring sheet of the present invention. The at least one secondary sheet may comprise an aperture with no spring element or other retention means, such that the aperture provides only support to the instrument. In such instances the at least one secondary sheet is referred to as a support sheet. Alternatively the at least one secondary sheet can comprise additional holding means for retaining the medical instrument. In such instances the at least one secondary sheet is preferably a spring sheet according to the present invention, such that the medical instrument is retained within the holding means of two or more spring sheets.

In a further embodiment, when the aperture of the holding means is open to a lateral edge of the spring sheet, a plurality of spring sheets are fixed to the base tray such that they protrude therefrom in a direction substantially perpendicular to the base tray and are spaced apart by a certain distance. Each spring sheet comprises at least one holding means in accordance with the present invention and at least one additional aperture open to a lateral edge of the spring sheet which has no retentive function. The spring sheets are arranged such that the holding means of one spring sheet is aligned with a non-retentive aperture of a second spring sheet. In this way a plurality of spring sheets can be used to support a plurality of medical instruments, the longitudinal axes of which are oriented more or less perpendicular to the planes of the spring sheets. Each instrument is housed within a plurality of spring sheets but is only retained by the holding means of one or a limited number of these spring sheets.

As well as fixing the above discussed vertically orientated sheet(s) to the base tray it is also possible for such sheets to be fixed to other components of the cassette. For example, the one or more spring sheets and optionally one or more support sheets can be fixed to the underside of the cover part. Alternatively or additionally the cassette may comprise an additional sheet held within the cassette parallel to the base tray. The above described vertical spring sheet(s) and support sheet(s) could also be attached to such an additional sheet.

In other embodiments the spring sheet is preferably located essentially parallel to the base tray, i.e. it is horizontally orientated within the cassette. In such embodiments the aperture of the at least one holding means preferably has a closed cross-section. The horizontal spring sheet is preferably removeably attached to the cassette such that the spring sheet can be removed to allow access to the base tray.

For instance, the spring sheet is preferably provided with at least one support leg which protrudes from the bottom surface of the spring sheet at an essentially right angle and which is intended to be positioned on the base tray. Supported by the at least one support leg, the spring sheet is thereby arranged essentially parallel to but at a distance to the base tray. This has the advantage that the base tray can be used to store additional instruments.

For providing a stable support, preferably at least three support legs are provided. In a particularly preferred embodiment, four support legs are provided, each of the support legs being attached to a respective corner of the spring sheet.

Additionally or alternatively the spring sheet can be placed directly on an upper rim of the base tray. In such embodiments the base tray comprises a planar base surface and four walls extending substantially vertically therefrom. The upper surface of these walls can provide a ledge on which the spring sheet can be supported essentially parallel to the base surface of the base tray.

In each of the above described preferred embodiments, it is further preferable that a stop surface is provided essentially parallel to and at a distance to the spring sheet for providing a physical stop to the medical instrument inserted through the holding means. This ensures correct positioning of the medical instrument within the holding means and helps to stabilise long instruments and prevent any tilting during transport and storage.

According to one embodiment the stop surface is formed by a part of the base tray. Preferably however it is formed by a separate metal or metal alloy stop sheet provided at a fixed distance with respect to the spring sheet. Therefore, the cassette preferably further comprises a metal or metal alloy stop sheet, which is provided essentially parallel to and at a distance to the spring sheet.

It is preferable that the stop sheet has the same footprint as the spring sheet, such that the stop sheet can provide a stop surface for holding means positioned at any location on the spring sheet.

The stop sheet may be a continuous surface or may also have at least one through-hole which is coaxially aligned with the passage to allow a portion of the medical instrument to be accommodated within the through-hole. Thus, if the medical instrument is provided with two adjoining portions of different cross-sections, in particular a first portion with a larger cross-section adjoined by a second portion with a smaller cross-section, an intermediate shoulder is formed on the medical instrument. This intermediate shoulder can then be used as a bearing surface that bears against the stop surface if the through-hole in the stop sheet has a larger diameter than the diameter of the second portion but a smaller diameter than the diameter of the first portion.

Additionally or alternatively a stop surface may also be provided in form of a pin or a post. A stop surface is then provided by the surface of the individual pin or post, which is aligned with and oriented essentially parallel to the cross-section of the passage. This design of stop surface has the advantage that the distance of the stop surface to the holding means can be varied, depending on the height of the pin or post. For instance, if the spring sheet comprises at least two holding means for holding at least two different medical instruments, the surface of a first pin or post can provide a first stop surface, which is aligned with the first holding means and positioned essentially parallel and at a first distance thereto, and the surface of a second pin or post can provide a second stop surface, which is aligned with the second holding means and positioned essentially parallel at a second distance thereto, wherein the first and the second distances are different from each other.

Such a stop pin or post can be attached to any suitable surface of the cassette, e.g. a base tray or cover part. However, it is preferable that the stop pin is located on a stop sheet. In this way both the surface of the stop sheet and the stop pin form stop surfaces for different medical instruments.

The stop sheet according to the present invention therefore is preferably a planar metal or metal alloy sheet comprising at least one pin, wherein the surface of the stop sheet and the surface of the pin facing the spring sheet form stop surfaces.

The stop sheet could be a metal or metal alloy sheet attached to the base tray or cover and extending essentially perpendicular thereto. Such a stop sheet can be used in combination with spring sheets orientated vertically within the cassette.

The use of a stop surface however is most beneficial in combination with a spring sheet orientated horizontally within the cassette, as it ensures that the instrument is not inserted too far through the holding means. This could result in the instrument touching or damaging any further instruments stored under the spring sheet, e.g. on a base tray.

In a preferred embodiment the cassette further comprises an intermediate sheet, comprising at least one guide hole which is coaxially aligned with the holding means and which is positioned essentially parallel and at a distance to the spring sheet, between the spring sheet and the stop sheet. Such intermediate sheets are of most benefit when the aperture of the at least one holding means of the spring sheet has a closed cross-section. The cross-section of the guide hole is adapted to be slightly larger than the cross-section of the medical instrument to be held within the holding means such that when correctly orientated the instrument can pass through the guide hole without contacting the intermediate sheet. Thereby the guide hole in the intermediate sheet provides axial guidance to the medical instrument during its insertion into the cassette. The medical instrument will pass through the guide hole in the intermediate sheet and come to rest on a stop surface of the stop sheet, e.g. the upper surface of the stop sheet or a pin or post fixed to this surface. By being held within the passage in the spring sheet and within the guide hole in the intermediate sheet, the medical instrument is securely held within the cassette at a predefined orientation. Thus, even if the cassette is shaken or tilted, the medical instrument does not easily become disengaged from the holding means and cannot assume a skewed position which may impede removal of the medical instrument.

In a preferred embodiment the at least one guide hole has polygonal cross-section, most preferably a triangular cross-section. When a circular cylindrical shaft of a medical instrument is inserted through such a hole, only points of surface contact can occur. In this way, even if the instrument contacts the guide hole for any reason, e.g. misalignment caused by shaking during transport, this contact is minimal and does not interfere with circulation of cleaning fluid past the instrument.

In a particularly preferred embodiment a spring sheet and stop sheet are connected together to form a sandwich unit which can be positioned and removed from the cassette as a single unit. A single cassette may contain one or more such sandwich units, each sandwich unit comprising the same or alternative configurations of spring and stop sheets, and optionally including one or more intermediate sheet, in accordance with the present invention. Preferably the components of the sandwich unit are permanently fixed together, for example by welding.

In a particularly preferred embodiment the sandwich unit comprises a spring sheet, intermediate sheet and stop sheet.

Such sandwich units can be removed from the cassette and positioned independently on a surface, while maintaining the order and sterility of the instrument(s) contained therein.

Preferably the sheets, i.e. spring, stop and optional intermediate sheet, of the sandwich unit are orientated horizontally within the cassette. In such embodiments the spring sheet preferably comprises one or more holding means comprising a closed aperture.

Preferably the sandwich unit comprises one or more support leg, each support leg preferably comprising two or more step changes in diameter, thus forming two or more intermediate shoulders on which the spring sheet, stop sheet and optional intermediate sheet(s) can be positioned at a fixed distance to one another. Preferably the sheets are welded to the intermediate shoulders of the one or more support legs. Support columns can optionally be provided between the sheets of the sandwich unit in order to provide additional support. Preferably four support legs are provided, one at each corner of the sandwich unit.

The support legs can be arranged to contact the base tray when the sandwich unit is housed within the cassette. Preferably the support legs are at least partially hollow in order to enable a complementary support post protruding from the base tray to be inserted. This ensures an accurate placement of the sandwich unit within the tray and prevents any sliding of the sandwich unit within the cassette.

The spring sheet of the present invention preferably includes a plurality of holding means according to the present invention, each suitable for retaining a medical instrument. The holding means can be identical in shape or be provided in a variety of shapes depending on designer choice and needs. The at least one spring element of each of the plurality of holding means can have different forms. For example a number of holding means can comprise tongue springs and a further number of holding means can comprise bridge springs. The tongue and bridge springs of different holding means may also have different shapes to one another. It is preferred that holding means designed to hold different instruments have different shapes. This assists the user in identifying the correct holding means for each instrument. Alternatively or in addition, the spring sheet can be provided with different colours or distinctive markings, such as letters, pictograms or numerals to identify each holding means. The clear distinction between different holding means allows fast and accurate assembly of the instruments within the cassette.

In addition, user information is preferably provided on the base tray and/or the spring sheet to assist in identifying the medical instruments and/or a correct sequence of medical instruments in a medical procedure. This reduces the time required to identify, clean, sort, count, and group medical instruments before, during or after a medical procedure.

When a plurality of holding means are provided in a spring sheet for retaining instruments of differing lengths, the intermediate sheet described above can also function as a secondary stop sheet. The surface of the intermediate sheet facing the spring sheet can form a stop surface and may alternatively or additionally comprise stop pins of the type described above. Further, the intermediate sheet can comprise through-holes for accommodating a part of the medical instrument having a smaller diameter than an adjacent portion, such that an abutment surface of the instrument rests against the intermediate sheet.

In addition to the holding means of the present invention it is also possible for the cassette to comprise additional holding means for a retaining a medical instrument.

For example, in a preferred embodiment the cassette further comprises one or more secondary holding means comprising a through-hole provided with an undercut, which undercut allows formation of a snap-fit connection to a complementary protrusion provided on the surface of the medical instrument. The undercut can be formed by an annular groove in the through hole or an annular protrusion, the undercut being created by the far side of the protrusion. In such embodiments the medical instrument comprises a complementary protrusion. At least the protrusion of the instrument (or, where present, the protrusion of the through hole) is resilient such that this can be deflected and/or compressed to allow the instrument to be inserted into the through hole until the undercut of the through hole and protrusion of the instrument are brought into alignment, whereupon the protrusion springs back to, or towards, its original shape. This provides the user with physical feedback that the instrument has been correctly inserted and the snap fit connection provides an axial retention between the holding means and the instrument.

The through hole may comprise a rib, which protrudes radially inwards into the space of the through-hole thus forming an undercut which is intended to engage to a protrusion, for instance a nub, rim or clamping ring, provided on the surface of the medical instrument, thereby creating a snap fit between the medical instrument and the through hole.

Alternatively, a groove may be provided on the interior wall of the through-hole to provide a snap fit connection to a medical instrument which has a protrusion, e.g. a nub, rim or clamping ring, on the outer surface of the instrument and protruding therefrom. The diameters of the through-hole and the medical instrument, as well as the dimensions of the undercut and the protrusion, are such that the instrument is held in place within the holding means when the protrusion of the instrument snaps into the undercut of the through hole.

The described snap fit construction allows a safe retention of the medical instrument in the through-hole, although only a small surface area of the medical instrument needs to be in contact with the contact surface.

In a preferred embodiment the one or more secondary holding means is formed on the spring sheet, in addition and separately to the at least one holding means. Preferably the one or more secondary holding means comprises a cylindrical extension piece having a through-bore comprising the undercut, which is welded or otherwise connected to the spring sheet such that it forms an extension of the spring sheet. This ensures a suitable thickness for forming the snap fit connection without unnecessarily thickening the entire spring sheet. Alternatively or additionally one or more secondary holding means can be positioned on the stop or intermediate plate.

In a similar manner to the spring element, such snap fit through-holes enable the cassette to hold one or more medical instruments without recourse to elastomeric components. Instead the holding means can be formed entirely of metal or metal alloy.

This is considered inventive in its own right and therefore, viewed from a further aspect, the present invention provides a cassette for storage of at least one medical instrument, the cassette comprising at least one holding means, the holding means comprising a through-hole provided with an undercut, which undercut allows formation of a snap-fit connection to a complementary protrusion provided on the surface of a medical instrument and wherein the holding means is made of a metal or a metal alloy.

Preferably the cassette further comprises a spring sheet as described above. Further preferred embodiments of this aspect are the same as those described above and below in relation to the first aspect.

In a further alternative, the holding means of the present invention can be adapted to retain a locking element of the cassette rather than a medical instrument. In this way the spring sheet provides an indirect retention to one or more medical instruments.

Such alternative holding means are particularly advantageous in cassettes in which the medical instruments are held within vertical spring sheets and/or vertical support sheets of the type described above, such that the instruments lie parallel to the horizontal plane of the cassette. In such embodiments the cassette preferably comprises one or more support sheet comprising one or more aperture shaped to accommodate a medical instrument and open to a lateral side of the support sheet, said sheet being orientated vertically within the cassette, the cassette further comprising a locking element which is moveable relative to the at least one support sheet which can be moved from a first position, in which it prevents the medical instrument from being removed from the at least one aperture, to a second position in which the medical instrument can be removed from the at least one aperture, the cassette further comprising retention means comprising an aperture defining a passage therethrough for holding a part of the locking element and a spring element positioned adjacent to said aperture for exerting a biasing spring force to retain the part of the locking element within the passage when the locking element is in the first position, thus preventing movement of the locking element into the second position.

In such embodiments the medical instruments are supported in apertures that do not comprise spring elements, such that the retentive force is provided by the locking element, which is retained by a spring element of the retention means. The retention means is preferably formed on the at least one support sheet, although it can be provided on another component of the cassette.

The locking element can be moved from the first to second position by, e.g. sliding the element relative to the cassette. Preferably however the locking element is connected to the cassette by a hinge, thus enabling the locking element to move from first to second position by rotation about the axis of the hinge.

In some embodiments at least one vertical spring sheet provides additional retention directly to one or more of the instruments. However, preferably the sole retention is provided by the locking element.

In order to assist with the cleaning process, it is preferable that the upper surface of the spring sheet and where present the stop sheet, the intermediate sheet, the base tray and/or the cover part is/are planar. A planar surface is easier to clean than one comprising grooves and protrusions, where dust and fluid can gather and which are difficult to clean effectively.

In a preferred embodiment the spring sheet comprises multiple additional holes to allow circulation of a cleaning medium. Preferably the spring sheet and, where present, the base tray, the cover part, the stop sheet and intermediate sheet and locking element are perforated such that a cleaning fluid, e.g. liquid or gaseous, can flow through the cassette, even in a closed state. Essentially it is preferred that all components of the cassette are perforated by fluid circulation holes. These fluid circulation holes allow the cassette with the at least one medical instrument stored therein to be cleaned, e.g. in an ACD machine, and then sterilized, e.g. in an autoclave.

Preferably the fluid circulation holes in adjacent sheets are offset from one another but provide a "line of sight" through the cassette.

In a particularly preferred embodiment a spring sheet is positioned essentially parallel to the base tray and a support sheet comprising a retention means, hereafter referred to as a retention sheet, is fixed to the base tray such that it protrudes therefrom in a direction towards the cover part. The at least one retention sheet may be fastened to the base tray, e.g. by welding, preferably such it protrudes therefrom at an essentially right angle, and the spring sheet is positioned above the at least one retention sheet. In particular, the distance of the spring sheet to the base tray is generally greater than the height of the retention sheet protruding from the base tray. Preferably the base tray comprises a plurality of support sheets attached thereto, the retention and support sheets forming vertical ribs extending from the base tray and the cassette further comprising at least one locking element. The spring sheet is preferably part of a removable sandwich unit comprising the spring sheet, an intermediate sheet and a stop sheet, or alternatively only the spring sheet and a stop sheet, which are welded or otherwise fixedly connected together such that these can be inserted and removed from the cassette as a single unit. Preferably the aperture of the at least one holding means has a closed cross-section. The sandwich unit may be positioned on at least one support leg, preferably at least three support legs, which is/are placed on one or more protruding support posts of the base tray to thereby hold the sandwich unit at a distance above the base tray.

The support leg(s) may be of the type described above comprising intermediate shoulders. Alternatively the support legs can be formed in one piece from the spring sheet, base tray or stop sheet. In a further alternative embodiment the sandwich unit is designed to rest on top of vertical walls of the base tray.

According to a particularly preferred embodiment, the cassette is a metal-only cassette, which means that all components of the cassette are made of metal or a metal alloy. Most preferably, the metal is stainless steel, aluminium or titanium as these metals have particularly suitable characteristics, such as durability, rigidity, stain-resistance, bacteria-resistant, chemical inertness and oxidation resistance. Preferably the one or more spring sheets of the cassette are formed of spring steel, in particular spring stainless steel, e.g. 1.4310s.

The cassette preferably comprises at least one medical instrument held within the holding means of the spring sheet, preferably at least one dental surgical tool for use in the placement of a dental implant. The dental surgical tool could be, for example, a drill, tap, insertion tool, mucosa punch etc. Preferably a plurality of such instruments are held within a plurality of holding means within the spring sheet.

FIGURES

Particularly preferred embodiments of the present invention are described below, by way of example only, and illustrated in the drawings in which purely schematically:

Figure 1:
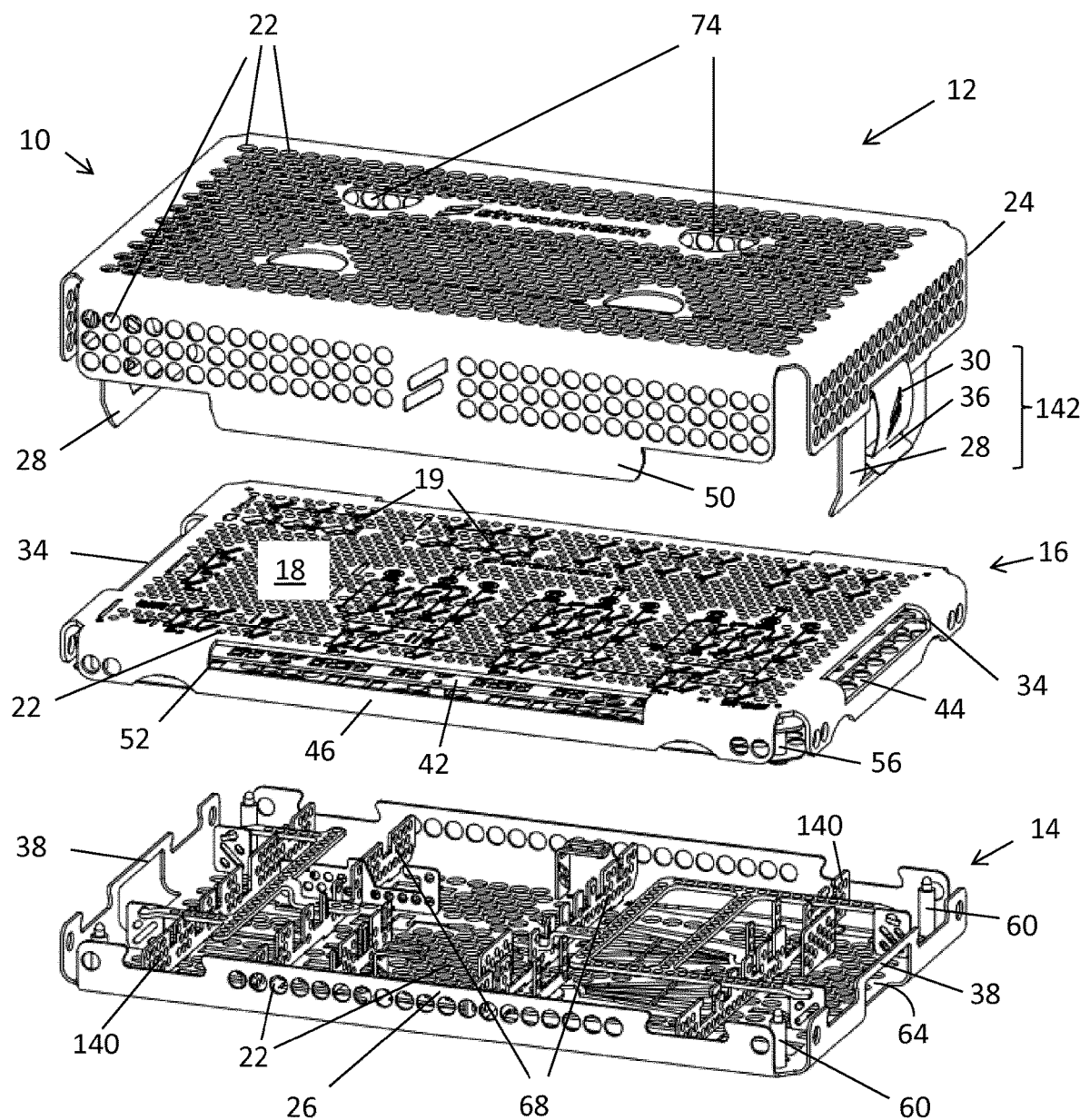
FIG. 1 shows in a perspective exploded view a first embodiment of the inventive cassette, in which a sandwich unit with a horizontal spring sheet is arranged between a cover part and a base tray, at a distance and parallel thereto.
Figure 3:
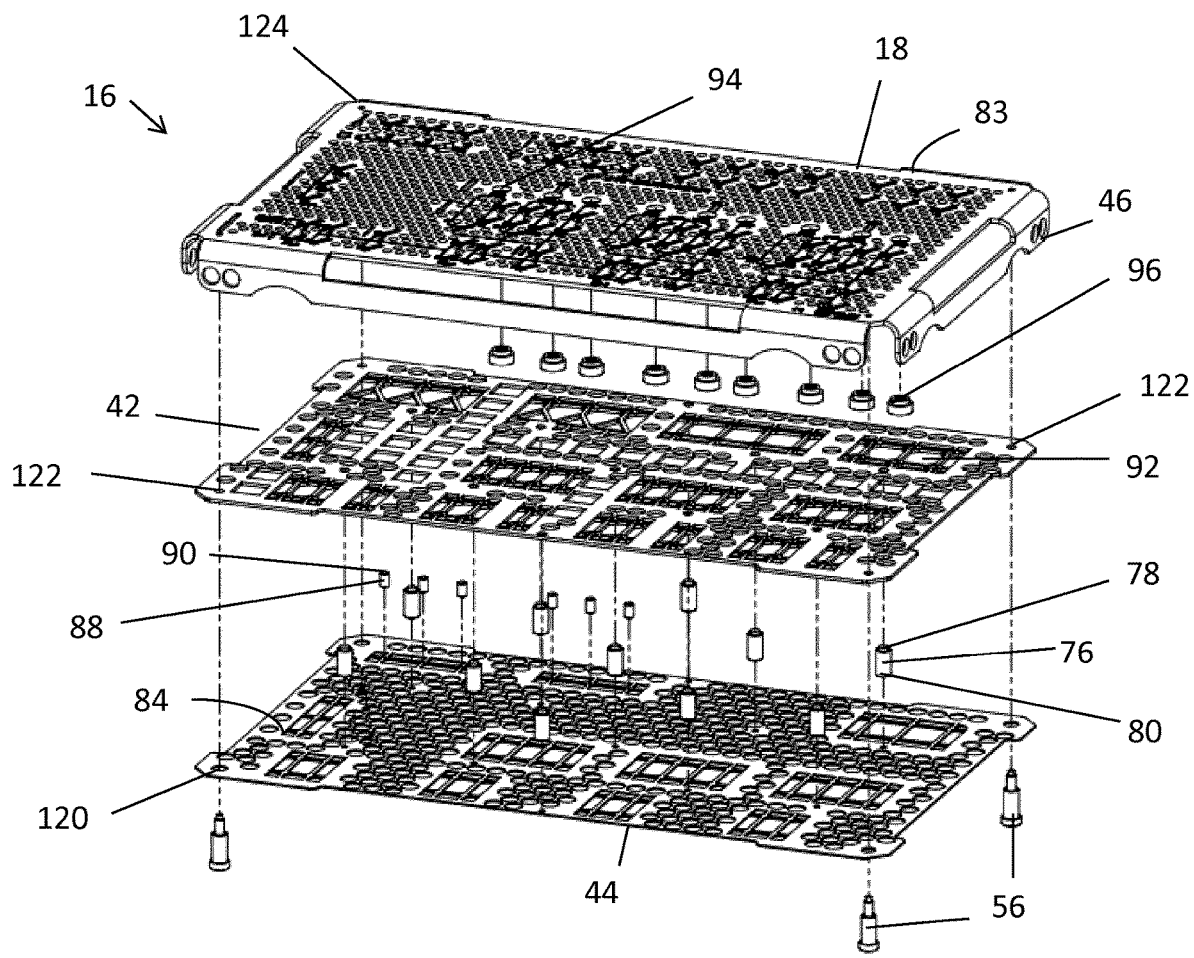
FIG. 3 shows in a perspective exploded view the sandwich unit of FIG. 1 with the horizontal the spring sheet, an intermediate sheet and a stop sheet which are arranged parallel and at a distance to each other.
Figure 4:
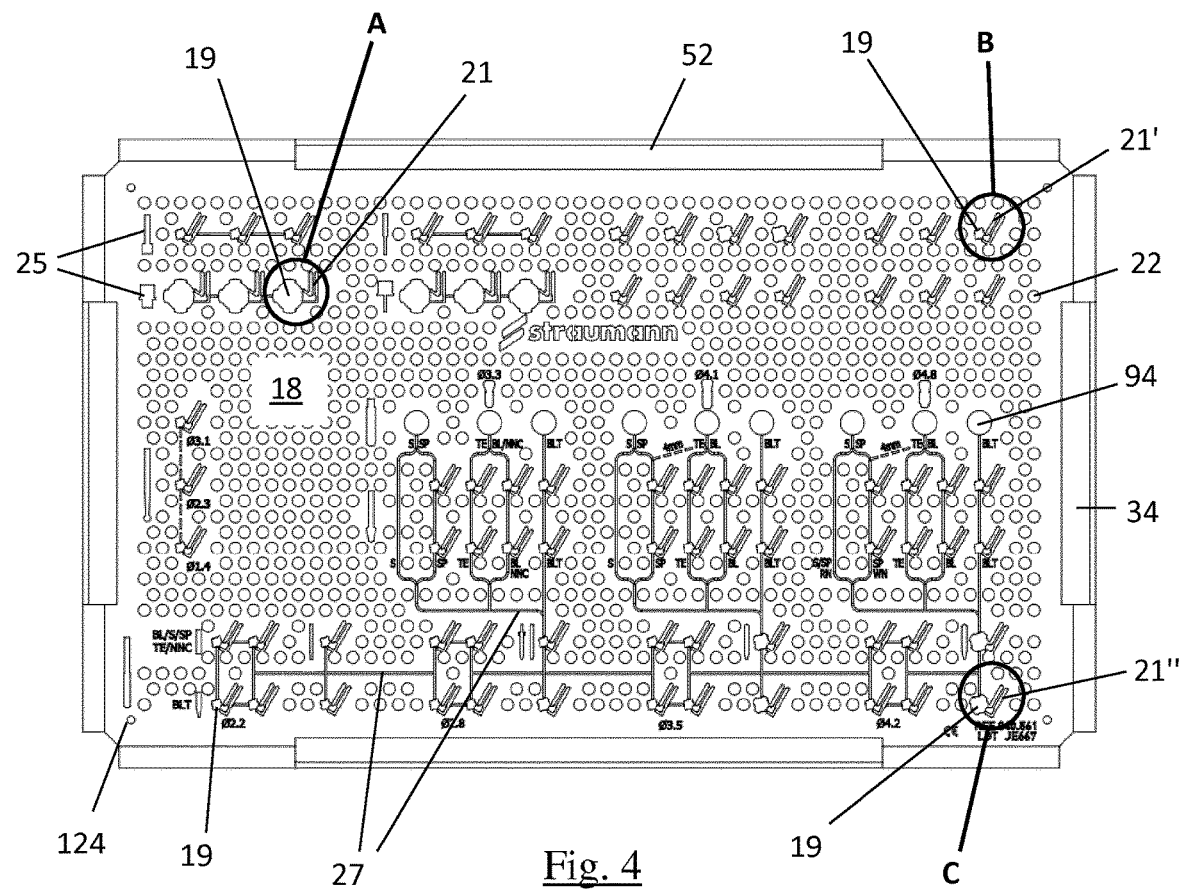
FIG. 4 shows a plan view of the spring sheet of FIG. 1 in isolation.
Figures 5A, 5B, 5C:
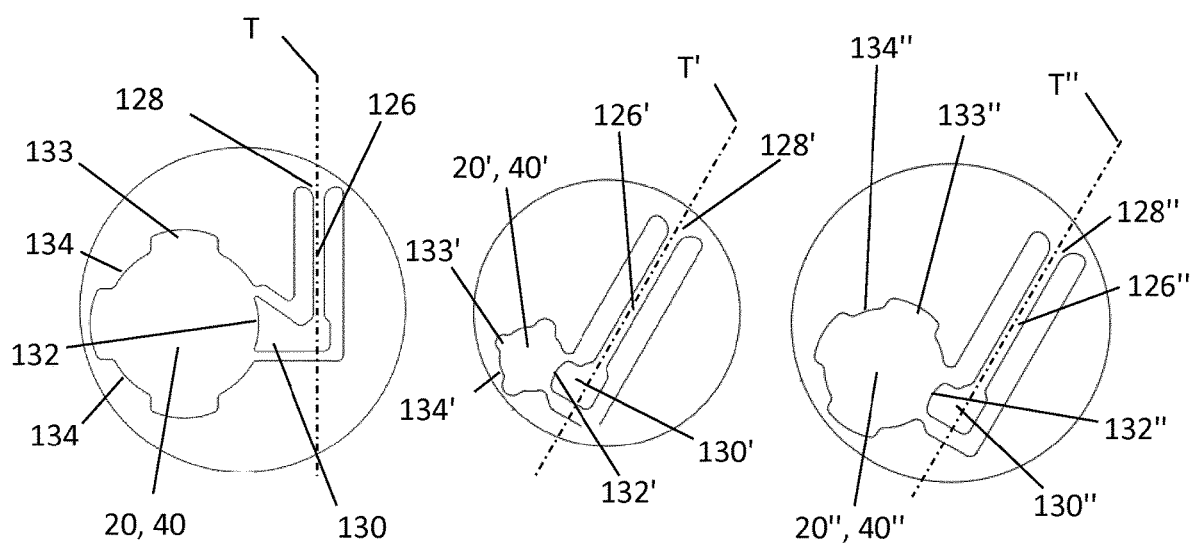
Figure 6:
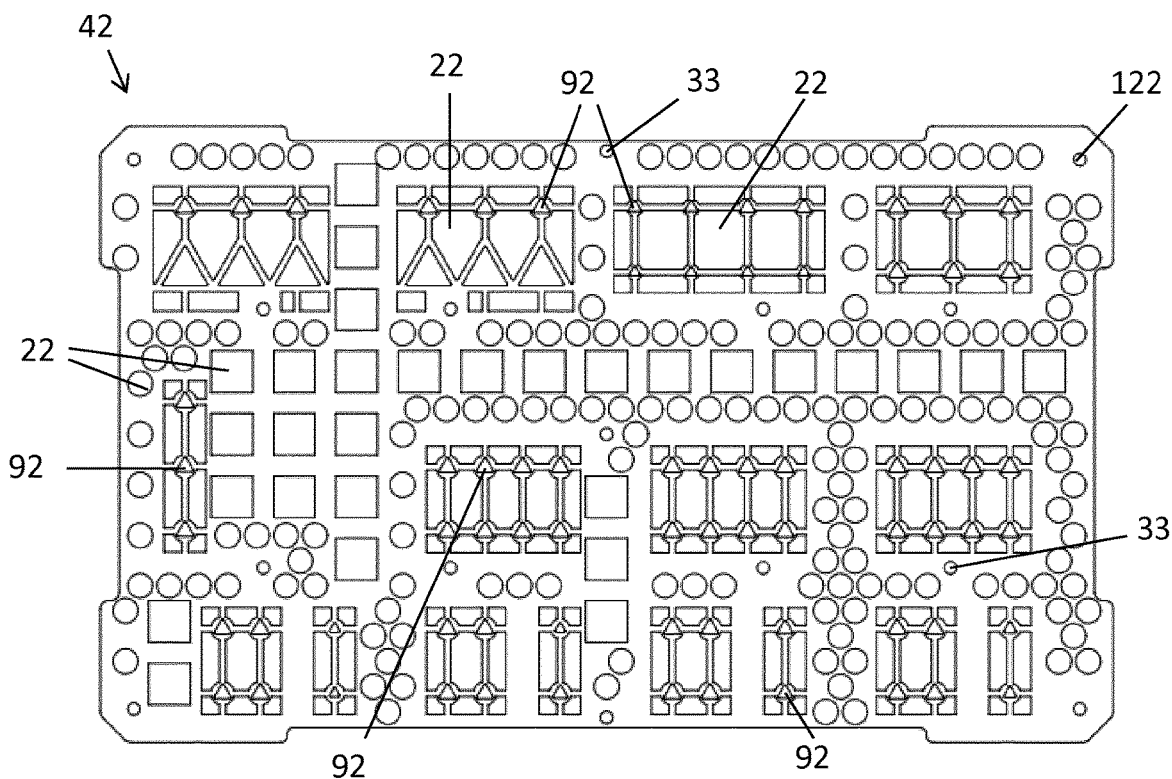
Figure 7:
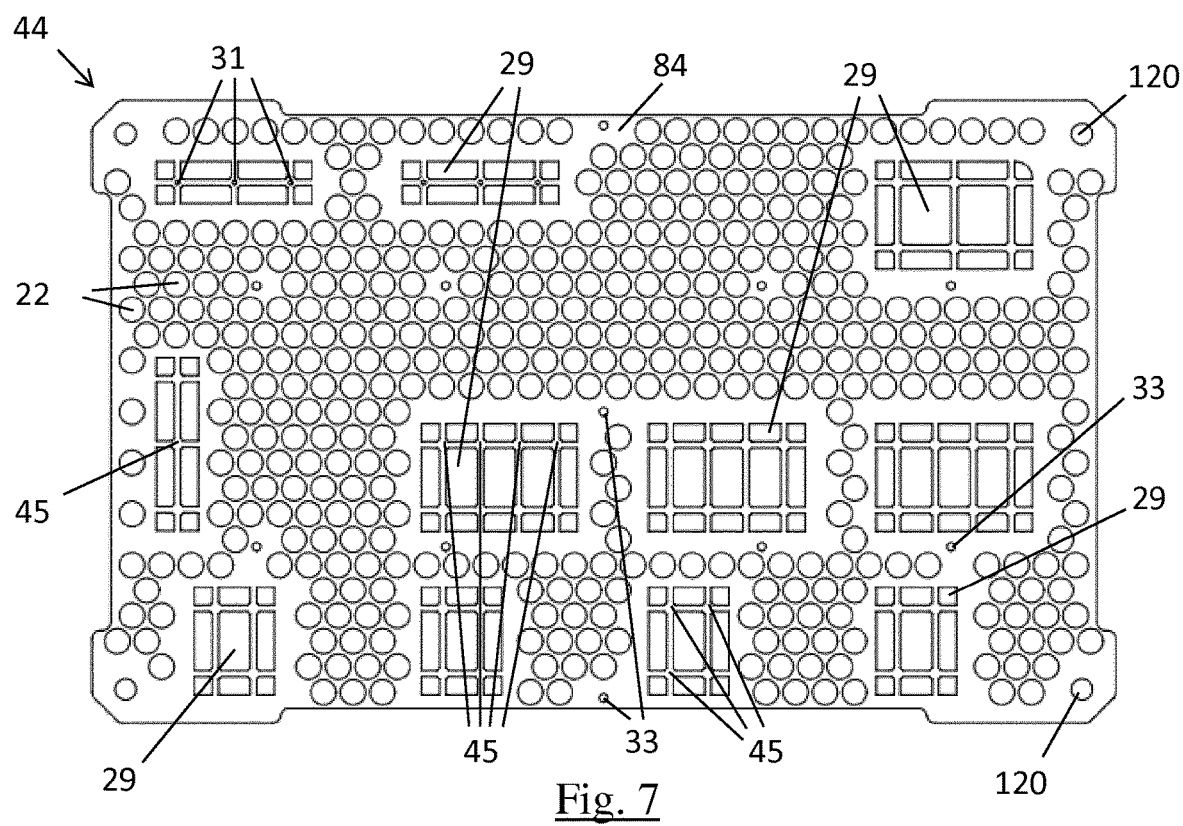
Figure 10A:
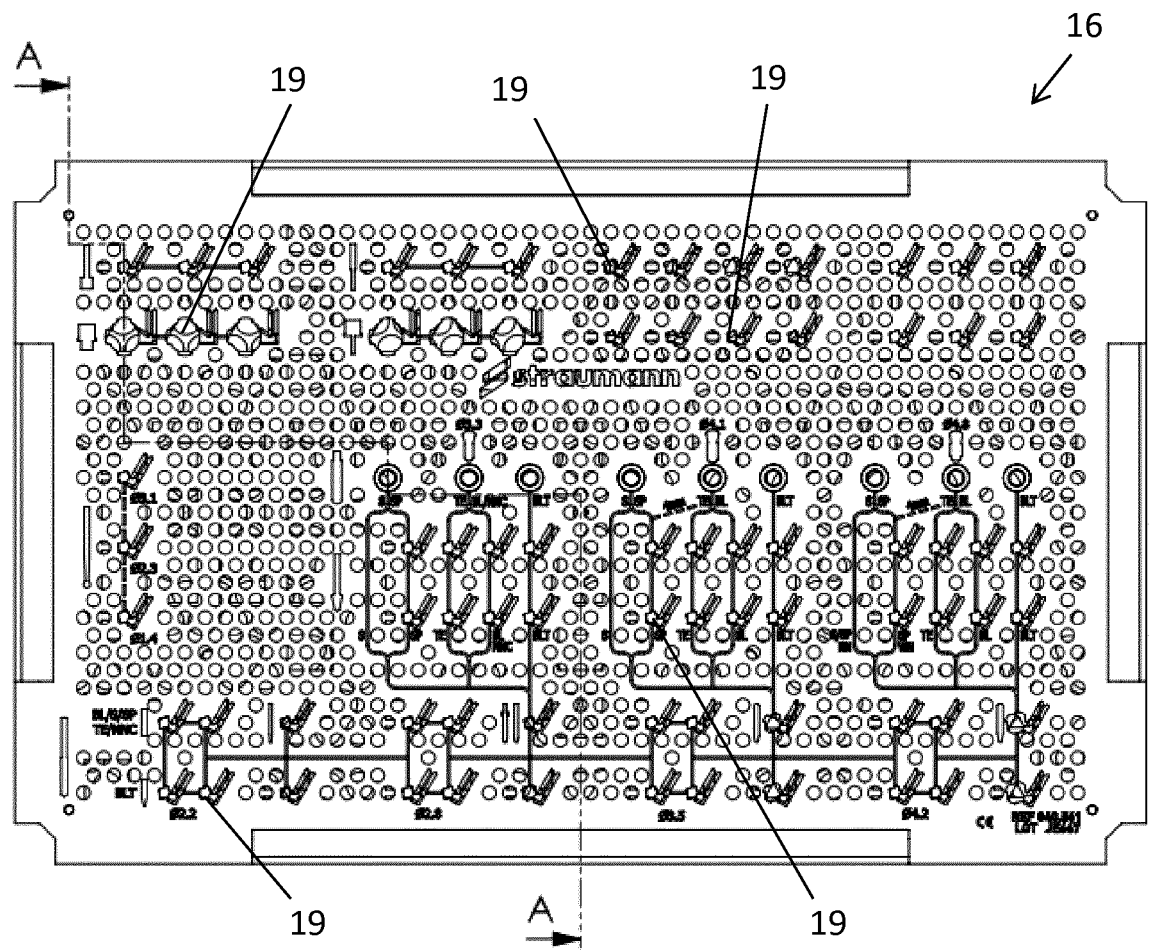
Figure 10B:
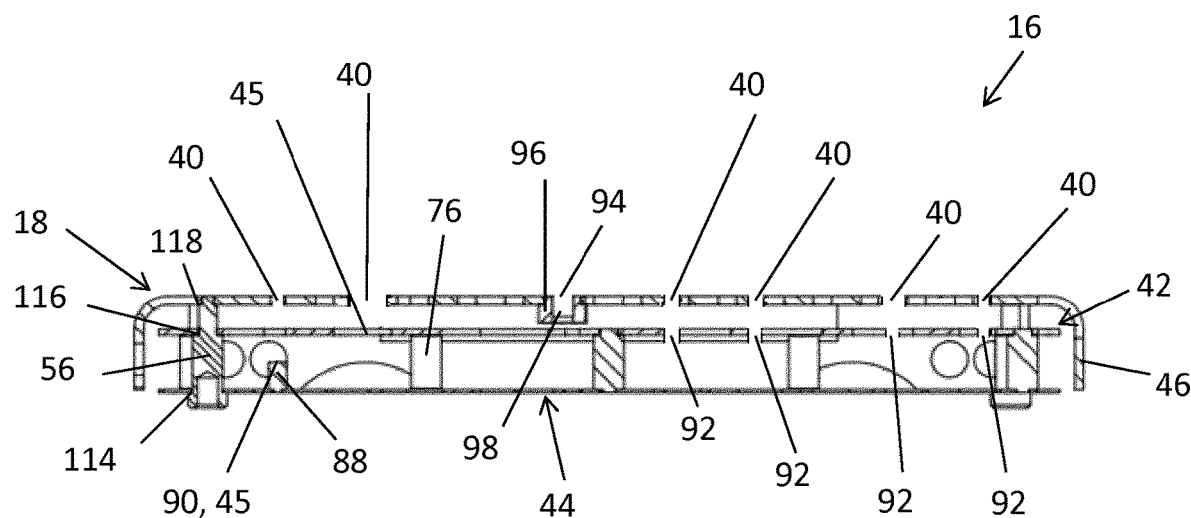
Figure 10C:
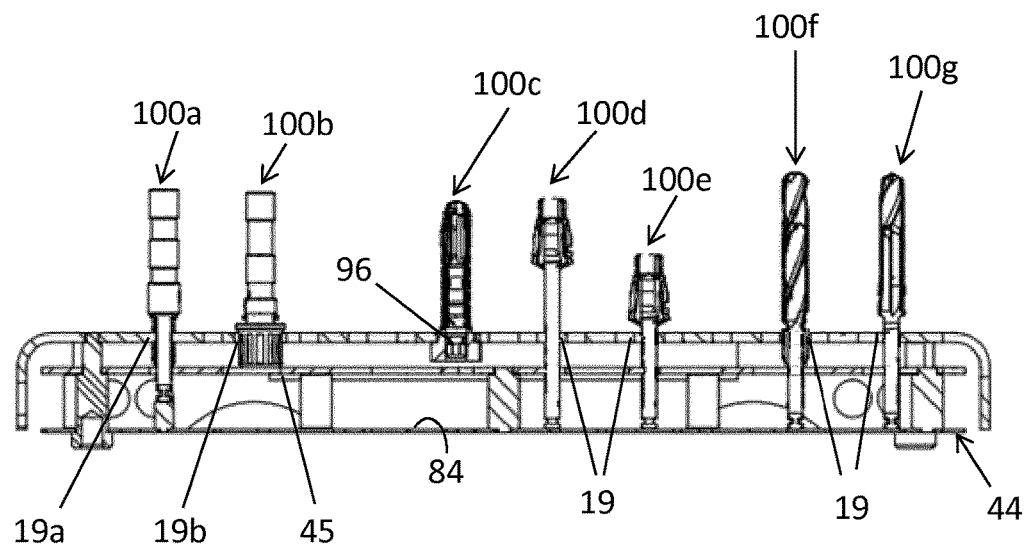
Figure 11:
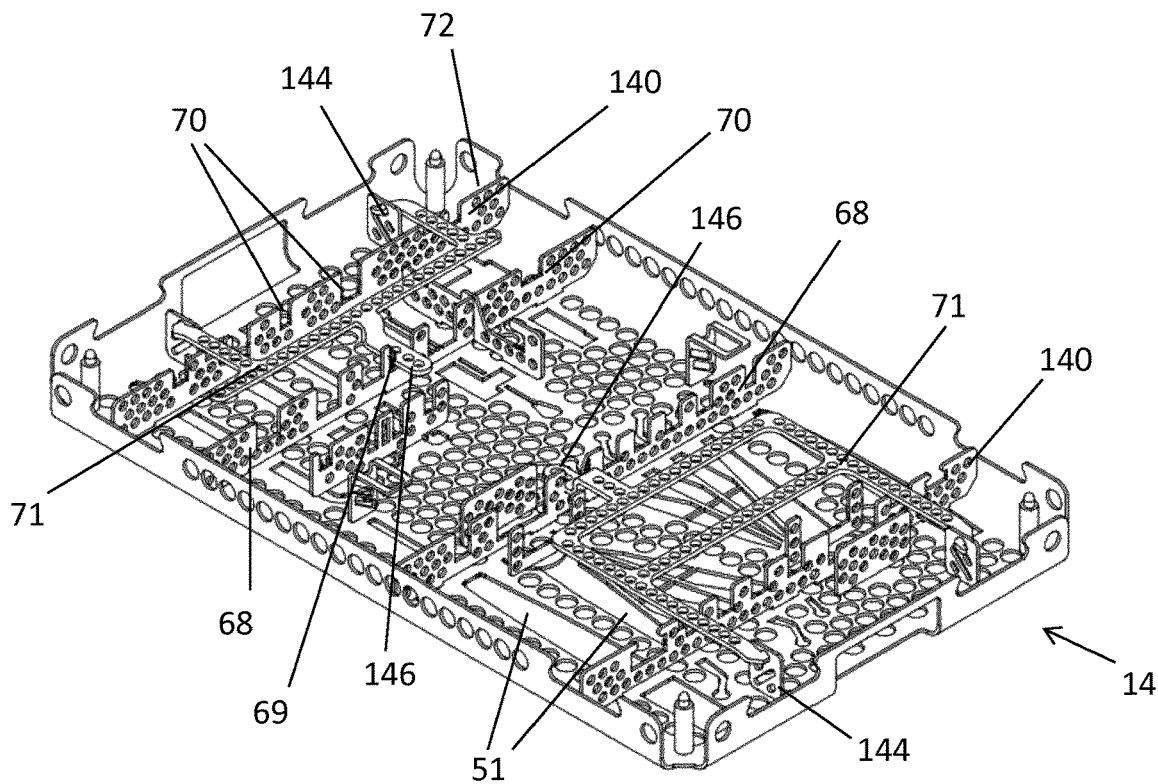
Figure 12:
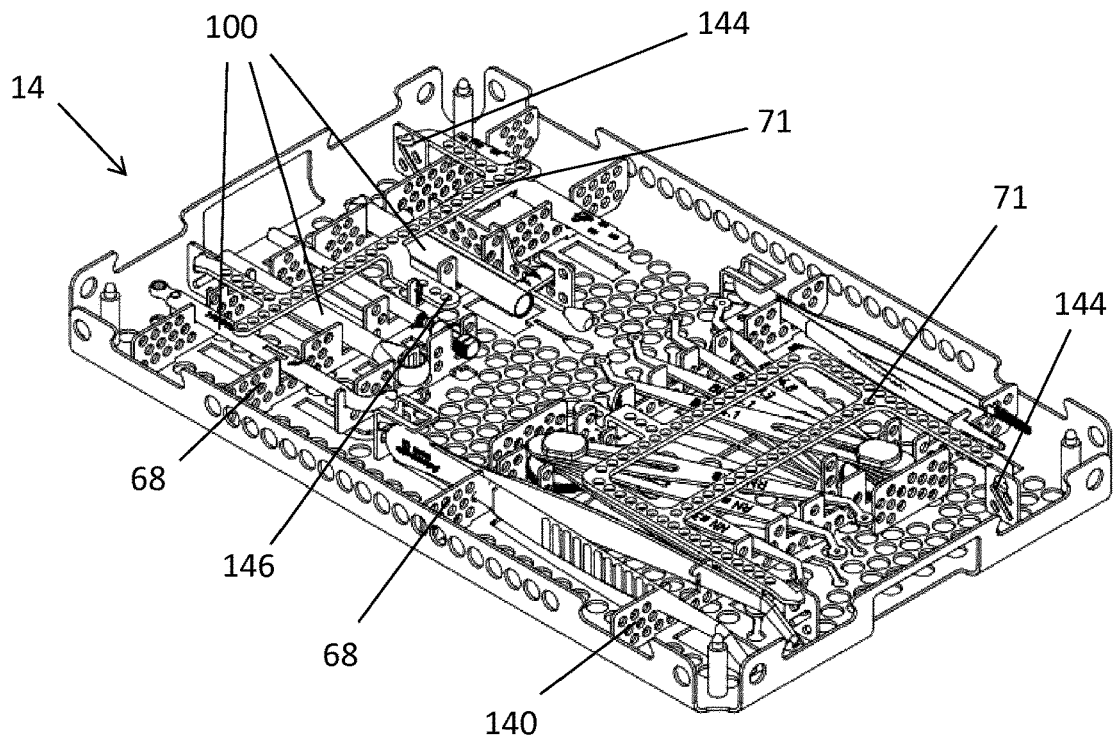
Figure 13:
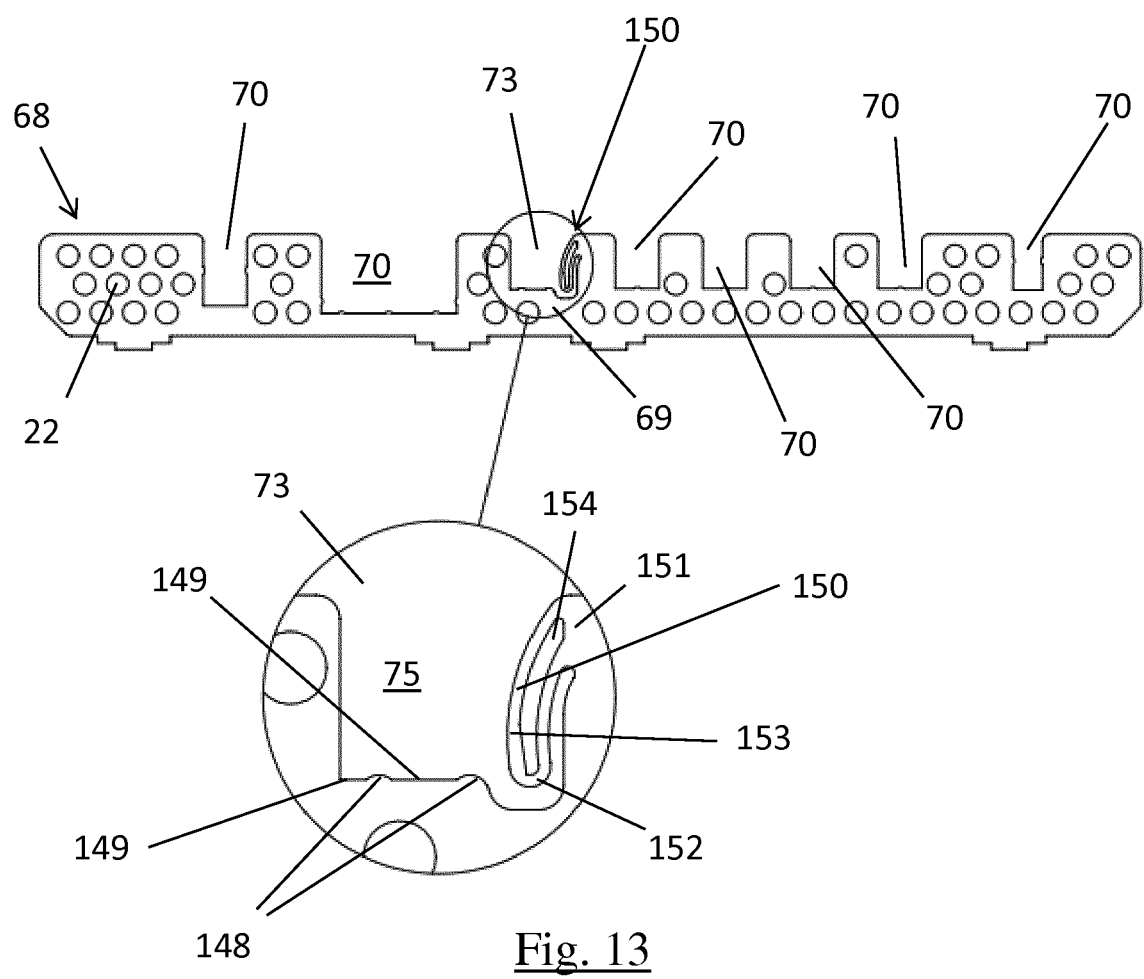
Figure 14:
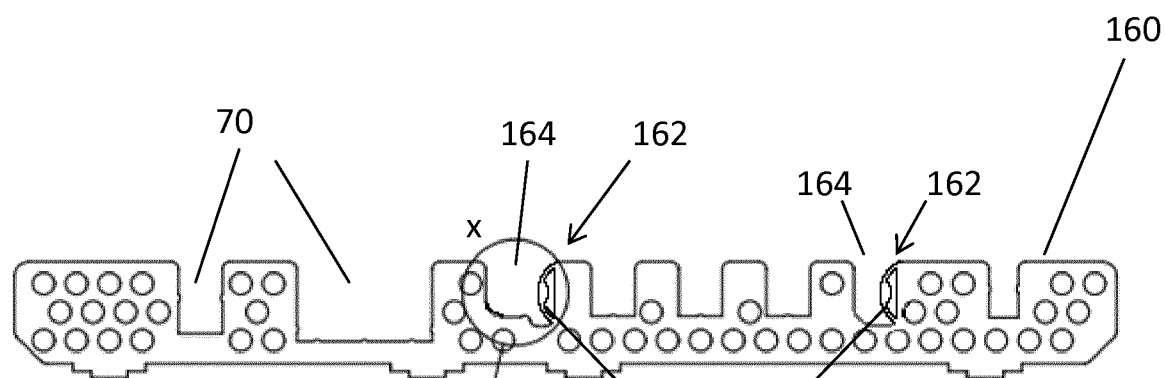
Figure 15:
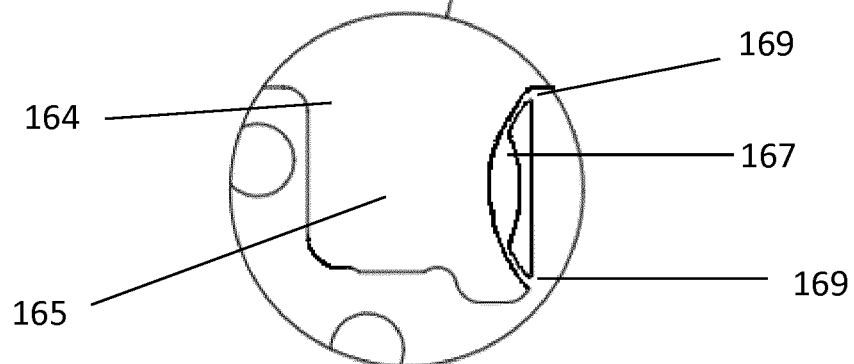
Figure 16:
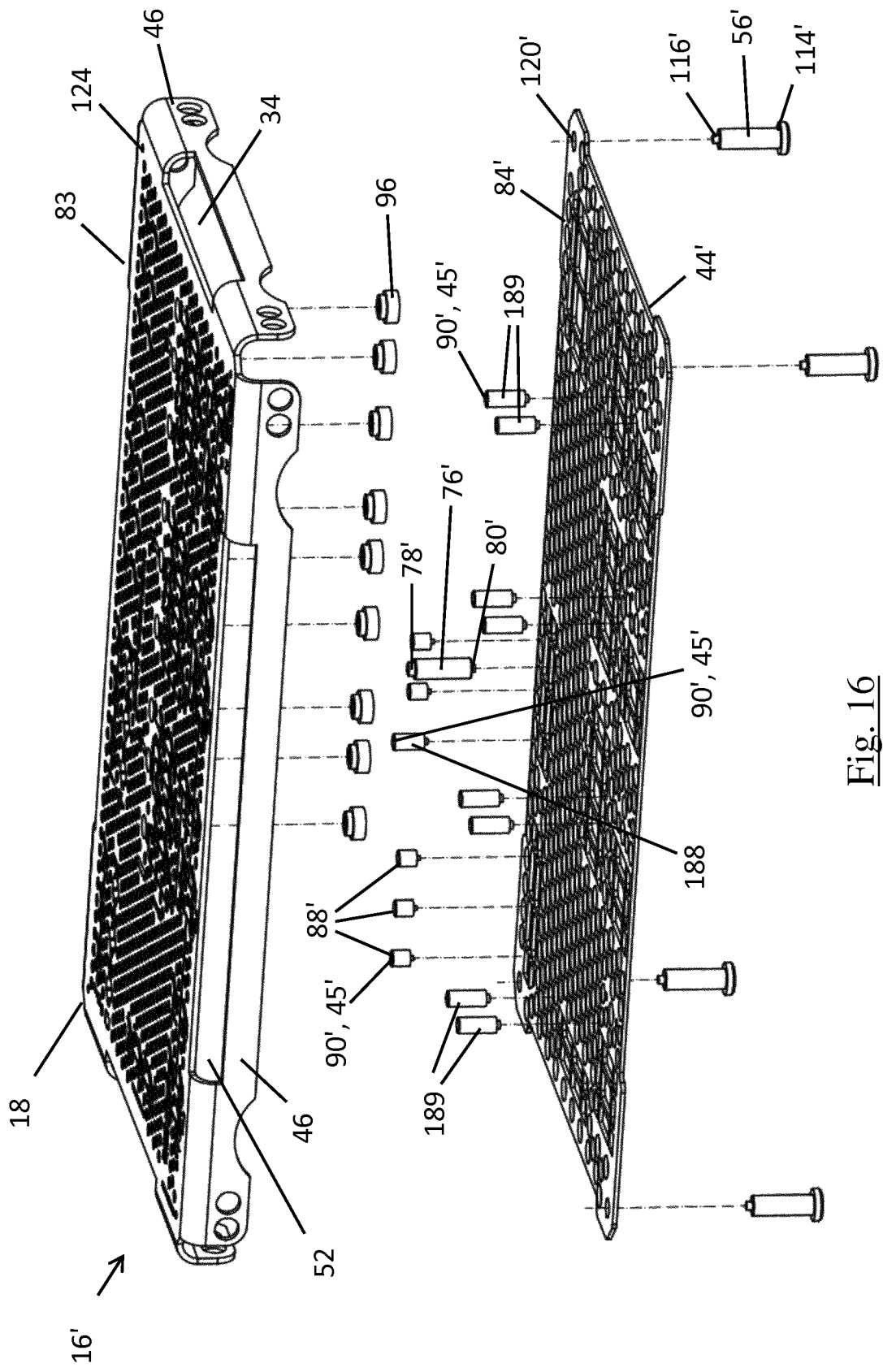
Figure 17:
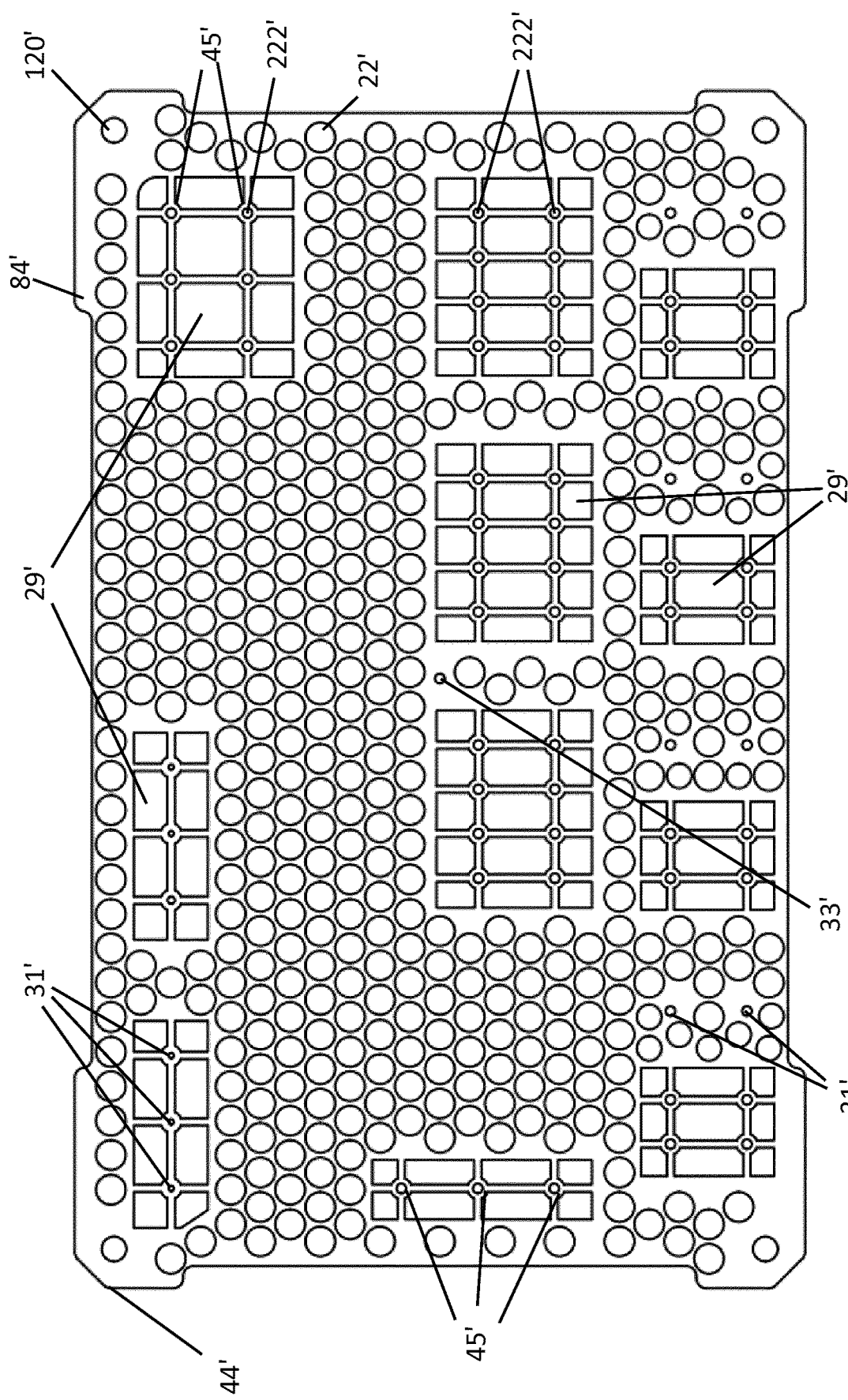
Figure 18:
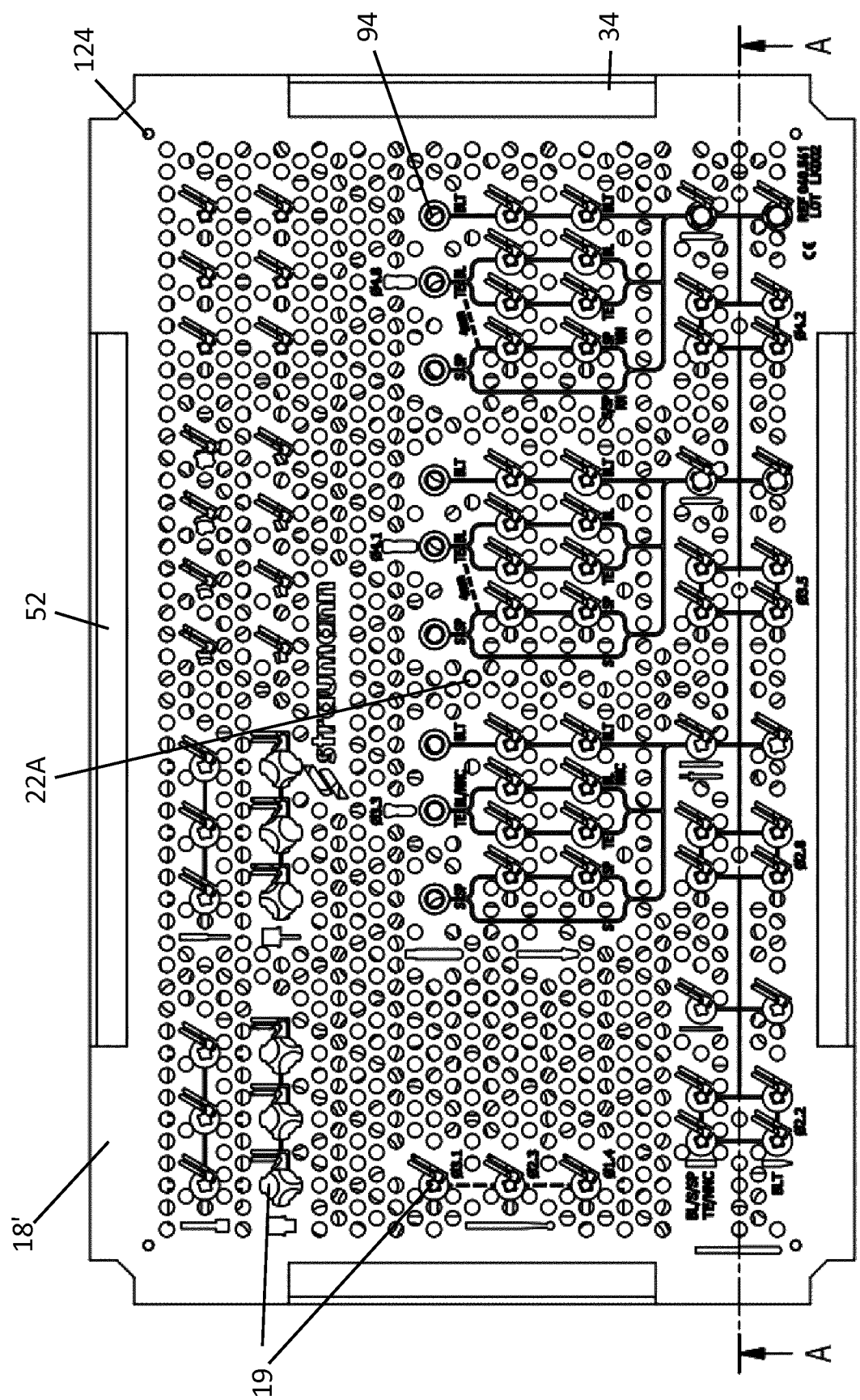
Figure 19:
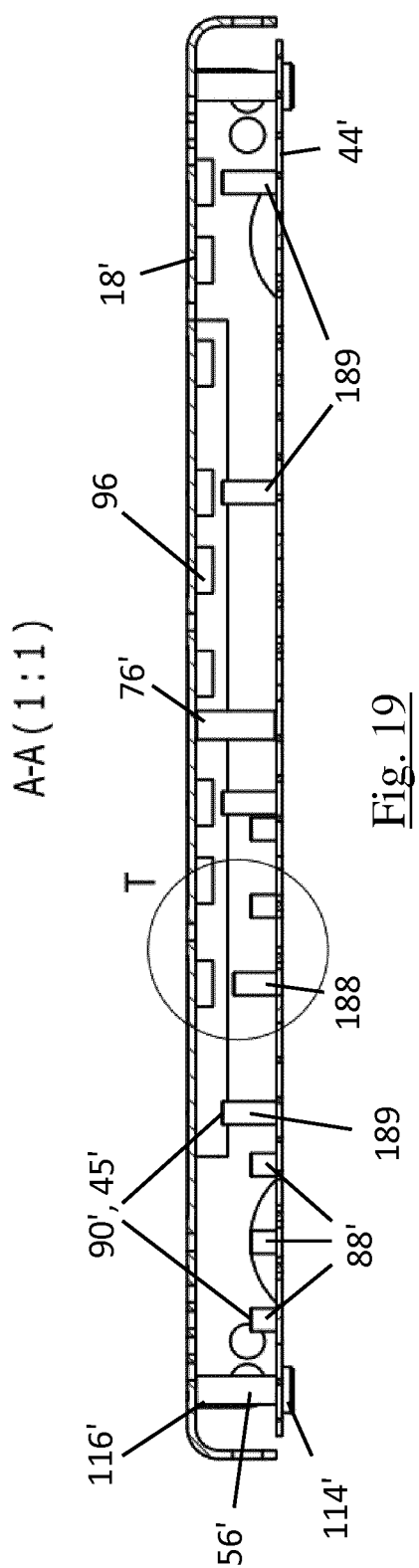
Figure 20:
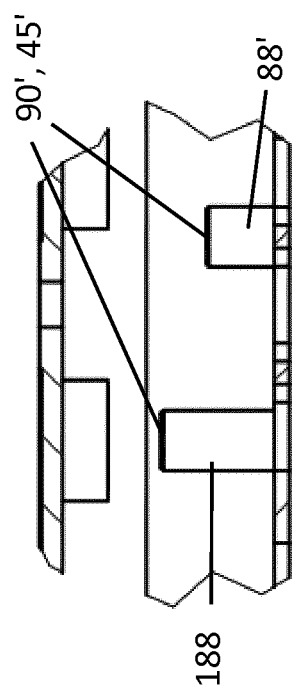

FIGS. 5A-C show in an enlarged top view the holding means enclosed by circles A, B and C of FIG. 4;

FIG. 6 shows a plan view of the intermediate sheet of FIG. 1 in isolation;

FIG. 7 shows a plan view of the stop sheet of FIG. 1 in isolation;

FIGS. 8A&B show a secondary holding means in cross-section and perspective view respectively;

FIG. 9 shows a cross-section of a support leg of the sandwich unit of FIG. 1;

FIG. 10A shows in a top view the sandwich unit of FIG. 3 in the assembled state;

FIG. 10B shows a vertical cross-section through the sandwich unit along line A-A of FIG. 10A;

FIG. 10C shows the vertical cross-section of FIG. 10B, but with a number of medical instruments arranged within the sandwich unit;

FIG. 11 shows in a perspective view the empty base tray of FIG. 1;

FIG. 12 shows the base tray of FIG. 11 with a plurality of medical instruments held therein;

FIG. 13 shows the retention sheet of FIG. 11 in isolation including an enlarged view of the retention means;

FIG. 14 shows a vertical spring sheet of the present invention positioned in an alternative embodiment of the base tray;

FIG. 15 shows detail X of FIG. 14;

FIG. 16 shows an exploded view of an alternative sandwich unit for use in the surgical cassette of FIG. 1;

FIG. 17 shows the stop sheet of FIG. 16 in isolation;

FIG. 18 shows a top plan view of the sandwich unit of FIG. 16;

FIG. 19 shows a cross-section through line A-A of FIG. 18;

FIG. 20 shows detail T from FIG. 19; and

FIG. 21 shows a cross-section through the longitudinal axis of a support leg of the sandwich unit of FIG. 16.

FIG. 1 shows an embodiment of the cassette 10 according to the present invention, wherein the cassette 10 comprises a metal cover part 12, a metal base tray 14 and a metal sandwich unit 16 that is enclosed between the former two parts. The cover part 12 and the base tray 14 form a box-like, essentially rectangular outer housing within which the sandwich unit 16 is housed.

For purposes of description herein, the terms "upper," "lower," "right," "left," "rear," "front," "vertical," "horizontal," and derivatives thereof shall relate to the cassette 10 as oriented in FIG. 1.

The sandwich unit 16 is removably insertable into the cassette 10 and includes a spring sheet 18 forming the horizontal top surface of the sandwich unit 16 and comprising numerous holding means 19, which are each intended to retain a medical instrument therein, as will be described in more detail below.

In the shown embodiment, the cover part 12 and base tray 14 are both boat-shaped and each includes a horizontally oriented, essentially rectangular planar surface as well as four side walls 24, 26, which project vertically downwardly and upwardly, respectively.

The cover part 12 and the base tray 14 are designed such that the cover part 12 can be releasably connected to the latter, enclosing the sandwich unit 16 with the medical instruments (not shown) for cleaning, sterilization, transport and storage. For securing the cover part 12 on the base tray 14, the former comprises closure elements 142, which are configured to couple with the base tray 14. More specifically, the cover part 12 comprises two closure elements 142 on each broadside, each comprising a larger C-shaped flap 28 and a smaller S-shaped spring latch 30. Each flap 28 is guided through a cutout 34 in the broadside of the spring sheet 18. The spring latches 30 have kinked free end portions 36 that are configured to snap into place underneath a bracket structure 38 formed on both broadside walls 26 of the base tray 14. Thereby, the cover part 12 can be clamped in position with respect to the base tray 14 and thereby securely hold the sandwich unit 16 there-between (see FIG. 2). It is to be noted that the closure element 142 can be any closure device or feature suitable to secure the cover part 12 to the base tray 14 and/or the sandwich unit 16 of the cassette 10.

In the embodiment of the cassette 10 shown in FIG. 1, the top surface of the sandwich unit 16 and the upper surface 64 of base tray 14 have an essentially rectangular shape and are essentially of the same size. In an alternative embodiment however the sandwich unit 16 may have a smaller footprint and be fully enclosed by the base tray 14 and cover unit 12 when the cassette is in the closed state.

The cover part 12 and the base tray 14 are both perforated, which means that they include a plurality of fluid circulation holes 22. The various components of the sandwich unit 16 also comprise fluid circulation holes 22. These permit circulation of a gaseous or liquid cleaning medium within and through the cassette 10 in the closed state. In particular, the fluid circulation holes 22 allow that the cassette 10 with the at least one medical instrument stored therein can be cleaned, e.g. in an ACD machine, and then sterilized, e.g. in an autoclave. The fluid circulation holes 22 in the cover part 12, sandwich unit 16 and the base tray 14 have various shapes and sizes, although the majority of the holes 22 are circular.

The sandwich unit 16 forms a removable tray comprising the horizontal spring sheet 18, an intermediate sheet 42 and a stop sheet 44 (see FIG. 3) which are welded or otherwise fixedly connected together such that these can be inserted and removed from the cassette 10 as a single unit. The spring sheet 18 comprises four side walls 46, which extend downwards from the edges of the horizontal spring sheet 18 in a skirt-like manner, such that the opposing side walls 46 are arranged parallel to one another. In the assembled state of the cassette 10 (shown in FIG. 2), the downwardly extending sidewalls 24 of the cover part 12 are aligned with the downwardly extending side walls 46 of the spring sheet 18 and with the upwardly extending side walls 26 of the base tray 14. In particular, the lower edges of the front and rear side walls 24 of the cover part 12 are provided with tab-like vertical protrusions 50, which are intended to fittingly extend into corresponding cut-outs provided the spring sheet 18. In this way, the side walls 24 of the cover part 12 and the side walls 46 of the sandwich unit 16 are secured and aligned with respect to each other in a simple manner. As discussed above, the left and right side walls 46 of the spring sheet 18 also comprise cut outs 34 to enable the C-shaped flaps 28 of the cover part 12 to extend through the sandwich unit 16 and contact the base tray 14.

For placing the sandwich unit 16 on the base tray 14, the sandwich unit 16 comprises four support legs 56, each of which being attached to a respective corner of the spring sheet 18 and protruding therefrom at an essentially right angle towards the base tray 14. The support legs 56 are configured to be positioned on the top of support posts 60 provided in each of the four corners of the base tray 14. By placing the support legs 56 on top of the support posts 60, the sandwich unit 16 can be removably positioned on the base tray 14 and aligned therewith, such that the side walls 22, 46 are aligned flush one above the other. As a result, the sandwich unit 16 is arranged essentially parallel to the base tray 14 and positioned at a vertical distance thereto. The base tray 14 can thus be used to store additional instruments. For this purpose, the base tray comprises a number of support sheets 140 and retention sheets 68, which will be discussed in detail in relation to FIGS. 11-13.

Figure 2:
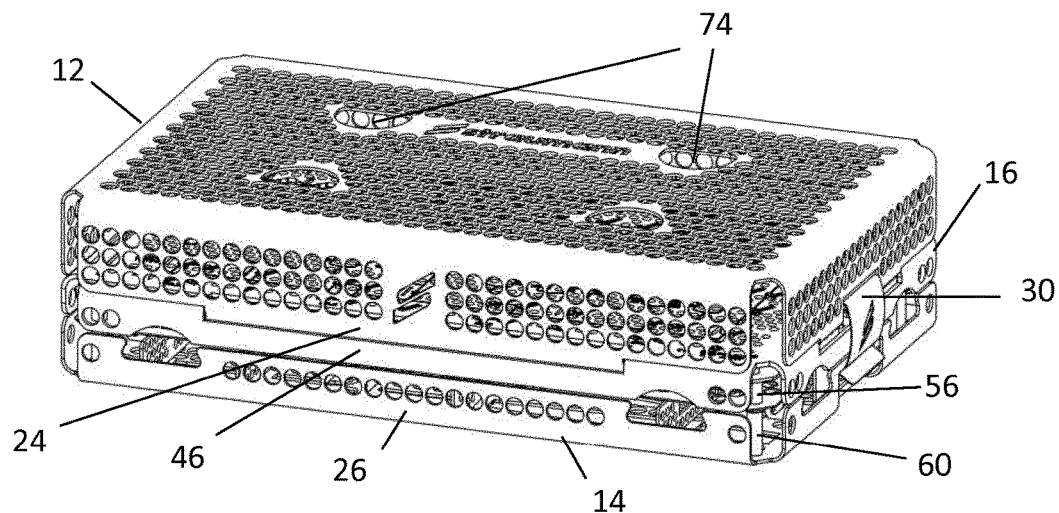
FIG. 2 shows a perspective view of the cassette of FIG. 1 in a closed state.

FIG. 2 shows the cassette 10 of FIG. 1 in the closed state, wherein the base tray 14 and the cover part 12 form a rigid, generally box-like outer housing defining a generally rectangular interior space in which the medical instruments are stored.

In the shown embodiment, the downwardly extending side walls 24 of the cover part 12 and the upwardly extending side walls 26 of the base tray 14 align with top edges and bottom edges respectively of the sandwich unit side walls 46.

As mentioned above, the cover part 12 comprises a pair of C-shaped flaps 28 and a pair of S-shaped spring latches 30, which are attached to the cover part 12. The spring latches 30 are pivotally mounted on the cover part 12 such they can pivot between a locking and non-locking position, in known manner. In the locking position, the spring latches 30 engage underneath the bracket structure 38 formed on both broad side walls 26 of the base tray 14.

Cover part 12 comprises four D-shaped cut-outs 74 in its planar top surface. These cut-outs 74 enable a user's fingers to be inserted therein to lift the cassette 10, e.g. out of a sterilisation container or transportation package. Thanks to the D-shaped cut-outs 74, no handle is required, which avoids areas of overlapping material and therefore facilitates cleaning and sterilization of the cassette 10.

FIG. 3 shows the sandwich unit 16 in an exploded view. The sandwich unit 16 is comprised of three sheets, namely spring sheet 18, intermediate sheet 42 and stop sheet 44. These three sheets 18, 42, 44 are all made of metal or a metal alloy and are welded or otherwise fixedly connected together such that the assembled sandwich unit 16 can be inserted and removed from the cassette 10 as a single unit. The spring sheet 18, intermediate sheet 42 and stop sheet 44 are held at a vertical distance to one another by means of the support legs 56 provided in each of the four corners of the sandwich unit 16. Additionally, support columns 76 are positioned between the intermediate sheet and the stop sheet 44 to further strengthen the sandwich unit 16 and maintain the distance between the intermediate sheet 42 and stop sheet 44. The support columns 76 have an upper end 78 that is fixed, e.g. by welding, to the intermediate sheet 42 and further have a lower end 80 that is fixed, e.g. by welding, to the stop sheet 44.

FIG. 4 shows a top view of the spring sheet 18 in isolation. From this view, it is clearly visible that the spring sheet 18 comprises a plurality of holding means 19 for retaining medical instruments. In addition the spring sheet 18 comprises numerous fluid circulation holes 22 as well as through-holes 94, the purpose of which will be discussed below in relation to FIGS. 8A and 8B. The top surface of the spring sheet 18 forms the upper surface of the sandwich unit 16 and is marked to assist the surgeon with identification of the instruments and the order or sequence of use of the medical instruments accommodated within the spring sheet 18. Pictograms 25 are provided to ensure the correct pairing of medical instrument and holding means 19 and lines 27 indicate the order of use of the instruments. The pictograms 25 and lines 27 can be provided on the spring sheet 18 by, e.g. silk printing.

As best seen in FIGS. 4 and 5A-C, the holding means 19, which are intended to accommodate and retain respective medical instruments therein, each comprise an aperture 20, 20', 20" with a closed cross-section forming a passage 40, 40', 40" and a spring element 21, 21', 21". The passages 40, 40', 40" in the spring sheet 18 are essentially circular, however in other embodiments they may have various other cross-sections, i.e. oval, rectangular, polygonal, etc.

In the shown embodiments, the spring elements 21, 21', 21" comprise a resilient metal tongue 126, 126', 126". More specifically, the tongues 126, 126', 126" of the spring elements 21, 21', 21" have an attachment end 128, 128', 128" and a free end 130, 130', 130" that is arranged at the opposing end of the tongue 126, 126', 126".

In order to retain an instrument within the holding means 19, the cross-section of the passage 40, 40', 40", in the plane of the spring sheet 18, is restricted by the adjacent respective spring element 21, 21', 21" to an extent that the medical instrument can only be inserted into the passage 40, 40', 40" under deformation of the associated spring element 21, 21', 21". Thus, the cross-section or diameter of the passage 40, 40', 40" is at least slightly smaller than the diameter of the medical instrument when the spring element 21, 21', 21" is in its resting position.

In the present embodiment, the spring elements 21, 21', 21" are integrally formed in one piece with the spring sheet 18. In this way, there is no join between the spring elements 21, 21', 21" and the spring sheet 18 into which bacteria, fluids, dirt etc. could enter, which allows a better cleaning. The spring element 21, 21', 21" can be prepared by cutting the spring sheet 18, e.g. by means of a water stream or laser cutting procedure.

In the shown embodiments, the cross-section of the passage 40, 40', 40" comprises at least three areas of contact surface for contacting the medical instrument. Said areas of contact surface are spaced apart from one another about the circumference of the passage 40, 40'. 40". A first area of contact surface 132, 132', 132" is formed by a surface of the free end 130, 130', 130" of the tongue 126, 126', 126" and at least two further areas of contact surface 134, 134', 134" are provided on the interior wall of the passage 40, 40', 40". The areas of contact surface 134, 134', 134" provided by the interior wall of the passage are concave arcs for contacting a circular cylindrical shaft of a medical instrument (not shown) and are interposed by recesses 133, 133', 133" which have a greater radius than the areas of contact surface 134, 134', 134". The recesses 133, 133', 133" provide areas about the passage 40, 40', 40" which in use do not contact the medical instrument, and hence create channels that allow a flow of cleaning fluid through the passage 40, 40', 40" even when a medical instrument is held therein. The area of contact surface 132 provided by the tongue 126 of FIG. 5A is also concave, however the contact surfaces 132', 132" of the tongues 126', 126" of FIGS. 5B, 5C are convex.

The area of contact surface 132, 132', 132" that is provided at the free end 130, 130', 130" of the tongue 126, 126', 126" of the spring elements 21, 21', 21" is angularly off-set from the central longitudinal axis T, T', T" of the tongue 126, 126', 126". More specifically, the location of the first area of contact surface 132, 132', 132" is such that its normal axis, i.e. the axis running perpendicular to the plane of the contact surface, is oriented at an angle of approximately 90° in relation to the longitudinal axis T, T', T" of the tongue 126, 126', 126". When the medical instrument is inserted into the passage 40, 40', 40" and brought into contact with, inter alia, the first contact surface 132, 132', 132", this angle enables the spring elements 21, 21', 21" to be deflected in the plane of the spring sheet 18 relative to the attachment end 128, 128', 128". This deflection of the spring element 21, 21', 21" (and the fact that the spring element aims to return to its resting position) results in the generation of the biasing spring force, by means of which the medical instrument is releasably retained within the passage 40, 40', 40" by friction fit. Said biasing spring force is such that it allows for securely yet releasably retaining the medical instrument within the aperture 20, 20', 20".

The different embodiments shown in FIGS. 5A-C illustrate that the shape and dimensions of the areas of contact surface 132, 132', 132" and 134, 134', 134" as well as of the areas of non-contact surface 133, 133', 133", can be adjusted to the shape and dimension of the medical instrument to be retained within the respective passage 40, 40', 40". The same applies for the shape and size of the tongue 126, 126', 126". In particular, the spring characteristics, in particular the bending properties of the tongue 126, 126', 126" can be adjusted by altering the length, width and/or the thickness of the tongue 126, 126', 126".

FIG. 6 shows the intermediate sheet 42 in isolation. The intermediate sheet 42 is positioned essentially parallel and at a distance to the spring sheet 18, between the spring sheet 18 and the stop sheet 44. The main purpose of the intermediate sheet 42 is to provide axial guidance to the medical instruments held in the holding means 19 of the spring sheet 18. The intermediate sheet 42 comprises multiple guide holes 92 coaxially aligned with the holding means 19 of the spring sheet 18. The cross-section of the guide holes 92 is adapted to be slightly larger than the cross-section of the medical instrument to be held within the associated passage 40 formed in the spring sheet 18. Thereby the guide holes 92 in the intermediate sheet 42 provide axial guidance to the medical instruments during their insertion into the sandwich unit 16. In the present embodiment the guide holes 92 have a triangular cross-section. Intermediate sheet 42 further comprises fluid circulation holes 22. These holes have varying cross-sections, e.g. circular, square, irregular etc. in order to enable maximum flow of fluid, particularly in the vicinity of the instruments within the guide holes 92, while still maintaining a suitable strength of the plate.

FIG. 7 shows stop sheet 44 in isolation. The main purpose of the stop sheet 44 is to provide a stop surface 45, i.e. a physical stop, which is intended to bear against an end face of the medical instrument inserted through one of the holding means 19 in the spring sheet 18. The stop surface 45 thereby ensures that the instrument is not inserted too far through the holding means 19, which could result in the instrument touching or damaging any further instruments stored under the spring sheet 18, e.g. on the base tray 14. In the shown embodiment, the stop sheet 44 has the same footprint as the spring sheet 18.

The stop surfaces 45 provided underneath the holding means in the spring sheet 18 are mostly formed by the top surface 84 of the stop sheet 44.

Some stop surfaces 45 are however also provided by pins 88 located on the stop sheet 44 (see FIG. 3). More specifically, these stop surfaces 45 are provided by a top surface 90 of the individual pin 88, which is aligned with and oriented essentially parallel to the cross-section of the associated passage 40. Thus, the top surface 84 of the stop sheet 44 and the top surfaces 90 of the stop pins 88 form stop surfaces 45 for different medical instruments. This has the advantage that the distances of the stop surfaces 45 to the holding means 19 in the spring sheet 18 can be varied, depending on the height of the pin 88. The stop pins 88 are welded to the stop sheet 44 at welding points 31. Further welding points 33 are provided on both the stop sheet 44 and intermediate sheet 42 for the attachment of the support columns 76 (see FIG. 10).

Stop sheet 44 also comprises numerous fluid circulation holes 22. As with the intermediate sheet 42, some of the holes have an irregular shape. These irregular holes 29 are positioned in order to allow maximum flow around the stop surfaces 45 and hence the medical instruments held there.

In use, the medical instrument will pass through the holding means 19 in the spring sheet 18, through an associated guide hole 92 in the intermediate sheet 42 and come to rest on an associated stop surface 45 of the stop sheet 44, e.g. the top surface 84 of the stop sheet 44 or the top surface 90 of a pin 88 fixed to this surface 84. In this way, the medical instrument is securely held within the cassette 10 at a predefined orientation (see FIG. 10C). Thus, even if the cassette 10 is shaken or tilted, the medical instrument does not easily get disengaged from the holding means 19 and cannot assume a skewed position which may impede removal of the medical instrument.

In this particular embodiment of the present invention the intermediate sheet 42 also functions as a secondary stop sheet. This will be described in more detail in connection with FIGS. 10B and 10C.

In the embodiment shown, the sandwich unit 16 not only comprises holding means 19 as described above but further comprises additional holding means for holding a medical instrument. More specifically, the spring sheet 18 comprises a number of through-holes 94—in addition and separately to the apertures 20 with the associated spring elements 21. Each through-hole 94 is aligned with a cylindrical extension piece 96 having a through-bore 98 and which is welded or otherwise connected to the underside of the spring sheet 18.

As shown in more detail in FIGS. 8A and 8B, extension piece 96 has through bore 98 provided with an annular protrusion 104 in an upper end area. Said protrusion 104 creates an undercut 105 that allows for the formation of a snap-fit connection to a respective protrusion, for example a clamping ring, provided on the outer surface of a medical instrument.

The spring sheet 18, intermediate sheet 42 and stop sheet are connected together by support legs 56. FIG. 9 shows a cross-sectional view of one of the support legs 56. As mentioned above in connection with FIG. 1, the support legs 56 are configured to be positioned on the top of support posts 60 provided in each of the four corners of the base tray 14. As can be seen from FIG. 9, the support legs 56 have a hollow space 109 in the bottom end 110. This enables the tip of the support posts 60 of the base tray 14 to be inserted into the support legs to fix the sandwich unit 16 to the base tray 14. The support legs 56 have a telescopic shape, i.e. a basic cylindrical shape, the diameter of which is reduced from a bottom end 110 towards a top end 112 in a step-like manner. With each reduction of the diameter of the support leg 56, a respective intermediate shoulder is formed. In the shown embodiment, the support leg 56 has three step changes, thereby forming a first shoulder 114 that is located in proximity to the bottom end 110, an second intermediate shoulder 116 and a third shoulder 118 that is located in proximity to the top end 112 of the support leg 56.

As shown in FIGS. 4, 6 and 7, each of the stop sheet 44, intermediate sheet 42 and spring sheet 18 comprise circular openings 120, 122, 124 in each of their corners. In analogy to the shape of the support legs 56, the size of the openings 120 in the stop sheet 44 are larger than the size of the openings 122 in the intermediate sheet 42 and the latter are again larger than the openings 124 in the spring sheet 18. In particular, the openings 120 in the corners of the stop sheet 44 are smaller than the diameter of the support leg 56 in the area of the bottom end 110 but larger than the diameter of the support leg 56 in the area of the second shoulder 116. As such, the openings 120 in the stop sheet 44 can be partly passed over the support legs 56 until the sheet rests on first shoulder 114. Similarly, the sizes of the openings 122 in the intermediate sheet 42 and the openings 124 in the spring sheet 18 are such that in the assembled state of the sandwich unit 16, the intermediate sheet 42 rests on the second intermediate shoulder 116 of the support legs and the spring sheet 18 rests on the third shoulder 118 of the support legs. The support legs 56 are welded in place to create the sandwich unit 16.

FIG. 10A shows a plan view of the assembled sandwich unit 16 and FIG. 10B shows a vertical cross-section through the sandwich unit 16 along line A-A of FIG. 10A. Here, the positioning of the intermediate sheet 42 that is sandwiched in between the horizontal spring sheet 18 and the stop sheet 44 can be clearly seen. Thus, the intermediate sheet 42 is arranged essentially parallel and at a distance to both of the spring sheet 18 and the stop sheet 44. One of the support legs 56 is also shown, illustrating that the stop sheet 44 rests on the first shoulder 114 of the support leg, the intermediate sheet 42 rest on the second intermediate shoulder 116 of the support leg and the spring sheet 18 rests on the third shoulder 118 of the support leg 56.

Support columns 76 can also be seen between the intermediate sheet 42 and stop sheet 44. In addition, stop pin 88 and extension piece 96 are visible. In the assembled state, the side walls 46 of the spring sheet 18 enclose the intermediate sheet 42 and end in approximate alignment with the stop sheet 44.

In cross-section it can clearly be seen that the passages 40 of the holding means 19 align with the guide holes 92 in the intermediate sheet 42 and stop surfaces 45 of the stop sheet 44, as is shown further below.

FIG. 10C shows the cross-section of FIG. 10B wherein medical instruments 100 are accommodated within the sandwich unit 16. Starting from the left, a first instrument 100a is held the holding means 19a and passes through a guide hole 92 in the intermediate sheet 42. With its front face, the medical instrument 100a rests on the top surface 90 of the stop pin 88. A second medical instrument 100b is held within the holding means 19b and rests with its front face on the top surface of the intermediate sheet 42. Thus in this embodiment the intermediate sheet 42 acts as secondary stop sheet. A third medical instrument 100c is held in snap fitting engagement with the extension piece 96. The further four medical instruments 100d-g shown in FIG. 10C are retained within holding means 19 in the spring sheet 18 and pass through guide holes 92 in the intermediate sheet 42 to rest with their front faces on the top surface 84 of the stop sheet 44.

FIG. 11 shows the base tray 14 of the cassette 10 in isolation. The base tray 14 comprises a plurality of support sheets 140 that are fastened to the base tray 14, e.g. by welding, such that they protrude therefrom in a direction substantially perpendicular to the base tray 14 and are spaced apart by a certain distance. The support sheets 140 therefore form vertical ribs extending from the base tray 14. Each support sheet 140 is provided with a plurality of apertures 70 which are open to a top edge 72 of the support sheet 140, namely that edge facing away from the base tray 14, such that a medical instrument 100 can be inserted laterally into the aperture 70, whereby the longitudinal axis of the instrument is oriented more or less perpendicular to the plane of the support sheet (see FIG. 12).

In addition, two retention sheets 68 are provided that are fastened to the base tray 14, e.g. by welding, such that they protrude therefrom in a direction substantially perpendicular to the base tray 14 and are spaced apart by a certain distance. The retention sheets 68 comprise further apertures 70, for holding the medical instruments and in addition a retention means 69 (see FIG. 13). The support and retention sheets 140, 68 are arranged on the base tray 14 such that at least some of the apertures 70 of one sheet 140, 68 are aligned with apertures 70 of a neighbouring sheet 140, 68. In this way, more than one sheet 140, 68 can be used to support one instrument—the longitudinal axes of which is oriented more or less perpendicular to the planes of the sheets 140, 68. This prevents the instrument from tilting along its longitudinal axis. With respect to the apertures 70 it is to be noted that these apertures 70 do not necessarily have to be identical in size and shape but can be adjusted independently from one another in accordance with the size and shape of the medical instrument to be received therein.

To securely hold the instruments within the apertures 70, locking elements 71 are provided. The locking elements 71 are moveable relative to the base tray 14 and sheets 140, 68 and are connected to the cassette 10 by a hinges 144, thus enabling the locking element 142 to move from a first to a second position by rotation about the axis of the hinge 144. In the first position, shown in FIGS. 11 and 12, the locking element 71 is in contact with or positioned just above the medical instruments held within the apertures 70, and thus prevents the medical instrument(s) from being removed from the apertures 70 in the sheets 140, 68. In the second position the locking element 71 is rotated about the hinge 144 such that it is remote from the medical instruments 100, which can then be removed from the apertures 70.

In the first position, a latch 146 of the locking element 71 is retained within retention means 69 of the retention sheet 68, which is shown in more detail in FIG. 13.

In FIG. 13, the retention sheet 68 is shown in isolation in a side view. Said retention sheet 68 comprises apertures 70 for supporting a plurality of instruments and additionally a retention means 69. The retention means comprises an aperture 73, forming a passage 75 for receiving the latch 146 of the locking element 71 and spring element 150. Spring element 150 is positioned adjacent to the passage 75 and restricts its diameter to an extent that the latch 146 can only be inserted into the passage 75 upon deflection and/or compression of the spring element 150 in the plane of the retention sheet 68.

This results in the spring element 150 applying a biasing force to the latch 146, thus retaining it within the passage 75. Retention means 69 is designed to retain the latch 146 of the locking element 142 within the aperture 73 when the locking element 142 is in the first position—in which removal of the medical instruments is prevented.

Spring element 150 is in the form of a tongue having an attachment end 151 integrally formed with the retention sheet 68 and an opposing free end 152. A contact surface 153 is formed on a lateral side of the tongue for contacting the latch 146. Spring element 150 further comprises a longitudinal slot 154 to increase the bending capacity of the element.

In addition nubs 148 are formed on the passage wall in order to provide contact surfaces for the latch 146. This creates areas of non-contact 149, which enable fluid to flow through the passage 75 even when latch 146 is retained therein.

As mentioned previously, base tray 14 is perforated by fluid circulation holes 22 in order to allow a good circulation of cleaning fluid. While the majority of these holes 22 are circular, the base tray 14 also comprises large cut-outs 51 in the shape of the instruments to be retained in the base tray 14. These function both as fluid circulation holes and a visual guide to the user showing the correct position for each instrument.

In an alternative embodiment the base tray 14 can comprise vertical spring sheets 160 having holding means 162 according to the present invention. An example of such a vertical spring sheet and holding means is shown in FIGS. 14 and 15.

The spring sheet of FIG. 14 comprises a plurality of apertures 70, 164 which open onto the upper side of the sheet 160. Some of these apertures 70 provide no axial retention and so simply provide support to the instruments positioned therein. A number of apertures 164 however form part of a holding means 162. These apertures 164 form a number of passages 165 through the sheet. Adjacent to the passages 165 are spring elements 167. These take the form of bridge springs which have an attachment end 169 at either end and protrude into the passage 165, thus restricting its cross-section. When an instrument 100 is inserted into the passage 165 the spring element 167 is deflected and/or compressed in the lateral direction of the sheet and thus provides a biasing force to retain the instrument within the holding means 162.

The spring sheet 160 of FIG. 14 can be welded to the base tray 14 in a similar manner to the support sheets 140 and retention sheets 68 of the main embodiment and provide direct retention to the instruments held therein. In an alternative embodiment the bridge spring of FIG. 15 could be adapted to cooperate with the latch 146 of locking element 71.

In an alternative embodiment, cassette 10 can comprise a sandwich unit comprising only a spring sheet and stop sheet, with no intermediate sheet. Such an alternative sandwich unit 16' is shown in FIGS. 16-21.

Sandwich unit 16' comprises a spring sheet 18' and stop sheet 44' with no intermediate sheet. The spring sheet 18' is identical to that described above and therefore the same reference numerals have been used to indicate the features of the spring sheet 18' which have previously been described in relation to spring sheet 18. In particular, spring sheet 18' comprises the holding means 19 previously described particularly in relation to FIGS. 4-5C and through holes 94 to which the cylindrical extension pieces 96 are welded or otherwise connected, as described in particularly relation to FIGS. 8A and B.

Stop sheet 44' is similar to that shown in FIG. 7. Stop surfaces 45' are provided underneath the holding means 19 in the spring sheet 18'. These are mostly formed by the top surface 84' of the stop sheet 44'. Some stop surfaces 45' are however also provided by pins 88', 188, 189 located on the stop sheet 44'. More specifically, these stop surfaces 45' are provided by a top surface 90' of the individual pin 88', 188, 189, which is aligned with and orientated essentially parallel to the cross-section of the associated passage. Thus, the top surface 84' of the stop sheet 44' and the top surfaces 90' of the stop pins 88', 188, 189 form stop surfaces 45' for different medical instruments. This has the advantage that the distances of the stop surfaces 45' to the holding means 19 in the spring sheet 18' can be varied, depending on the height of the pins 88', 188, 189.

In comparison to the stop sheet 44 of FIG. 7 the stop sheet 44' of FIG. 17 comprises a greater number and variety of stop pins. These additional stop pins 180, 189 have a greater length than stop pins 88', and provide a stop surface for tools that in other embodiments may be supported by the intermediate sheet. FIGS. 19 and 20 more clearly show the different heights of the stop pins 88', 188, 189 and how these enable different lengths of instrument to be supported. Each stop pin 88', 188, 189 is located under a holding means 19. The extension pieces 96 are not aligned with the stop pins as the extension pieces 96 provide an inbuilt axial stop in the form of the snap connection discussed above.

The stop pins 88', 188, 189 are welded to the stop sheet 44' at welding points 31'. A further welding point 33' is provided on the stop sheet 44' for the attachment of a support column 76', which will be discussed below.

Stop sheet 44' also comprises numerous fluid circulation holes 22', some of which have an irregular shape. These irregular holes 29' are positioned in order to allow maximum flow around the stop surfaces 45' and hence the medical instruments held there. Further, stop sheet 44' comprises additional fluid circulation holes 222 at the centre of each stop surface 45' formed on the top surface 84' of the sheet. These enable sterilisation fluid to contact the end of the medical instrument abutting the surrounding stop surface 45'. In some embodiments the instruments may enter the fluid circulation holes 222 for better centring and stability. The fluid circulation holes 22' of the stop sheet 44' and 22 of the spring sheet 18' are offset from one another but provide multiple lines of sight through the sandwich unit 16', as can be seen in FIG. 18.

In a similar manner to sandwich unit 16, alternative sandwich unit 16' also comprises a support column 76', however in this embodiment only a single column is provided which extends between the spring sheet 18' and stop sheet 44'. Welding point 33 is provided on the stop sheet 44' for attachment of the lower end 80' of this column 76' while the support column 76' is welded at its upper end 78' to the spring sheet 18' using one of the fluid circulation holes 22A, see FIG. 18. The support column 76' helps to maintain the correct distance between the stop and spring sheets.

With the removal of the intermediate sheet the design of the support legs 56' is simplified. The support legs 56' of the alternative embodiment are shown in detail in FIG. 21 and comprise only two shoulders, for welded attachment of the spring sheet 18' and stop sheet 44'.

In an analogous manner to the first embodiment, the support legs 56' are configured to be positioned on the top of support posts 60 provided in each of the four corners of the base tray 14. As can be seen from FIG. 21, the support legs 56' have a hollow space 109' in the bottom end 110'. This enables the tip of the support posts 60 of the base tray 14 to be inserted into the support legs to fix the sandwich unit 16' to the base tray 14. In contrast to the support legs 56 of the last embodiment, hollow space 109' is tapered to assist in the centering of the legs 56' over the support posts 60 to ease correct positioning of the sandwich unit 16' within the cassette 10. The support legs 56' have a telescopic shape, i.e. a basic cylindrical shape, the diameter of which is reduced from a bottom end 110' towards a top end 112' in a step-like manner. With each reduction of the diameter of the support leg 56', a respective intermediate shoulder is formed. In this embodiment, the support leg 56' has two step changes, thereby forming a first shoulder 114' that is located in proximity to the bottom end 110', and a second shoulder 116' that is located in proximity to the top end 112' of the support leg 56'.

As shown in FIGS. 17 and 18 respectively, the stop sheet 44' and spring sheet 18' comprise circular openings 120', 124 in each of their corners. In analogy to the shape of the support legs 56', the size of the openings 120' in the stop sheet 44' are larger than the size of the openings 124 in the spring sheet 18'. In particular, the openings 120' in the corners of the stop sheet 44' are smaller than the diameter of the support leg 56' in the area of the bottom end 110' but larger than the diameter of the support leg 56' in the area of the second shoulder 116'. As such, the openings 120' in the stop sheet 44' can be partly passed over the support legs 56' until the sheet rests on first shoulder 114'. Similarly, the size of the openings 124 in the spring sheet 18' are such that in the assembled state of the sandwich unit 16' the spring sheet 18' rests on the second shoulder 116' of the support legs as can be seen in FIG. 19. The support legs 56' are welded in place to create the sandwich unit 16'.

The above described embodiments are for illustrative purposes only and the skilled person will realize that alternative arrangements are possible which fall within the scope of the claims. For example, vertical spring sheets can be positioned on other components of the cassette, such as the cover sheet or horizontal spring sheet. One or more further sandwich units can be positioned within the cassette, e.g. above the existing sandwich unit or the shape of the sandwich unit can be altered such that two or more sandwich units can be positioned side-by-side within or above the base tray. The composition of the sandwich unit(s) can vary and of course a horizontal spring sheet can be used independently within the cassette. In addition a bridge spring of the type shown in FIG. 15 could be used in a horizontal spring sheet or retention means.

The invention claimed is:

1. A cassette for storage of at least one medical instrument, the cassette comprising:
   at least one spring sheet comprising at least one holding means for retaining the medical instrument therein, the holding means comprising:
      an aperture forming a passage through the spring sheet for receiving the medical instrument, and
      at least one spring element provided adjacent to the passage for exerting a biasing spring force to retain the medical instrument within the passage, the at least one spring element being integrally formed in one piece with the spring sheet,
   wherein the spring sheet, including the holding means, is made of a metal or a metal alloy.

2. The cassette according to claim 1, wherein the spring sheet is planar.

3. The cassette according to claim 1, wherein the cross-section of the passage comprises two or more areas of contact surface for contacting the medical instrument, one of the contact surfaces being formed by a surface of the at least one spring element and the contact surfaces being spaced apart from one another about the circumference of the passage.

4. The cassette according to claim 1, wherein the at least one spring element extends the length of the passage.

5. The cassette according to claim 1, wherein the at least one spring element comprises a tongue having an attachment end connected to the spring sheet and a free end arranged at the opposing end of the tongue, the tongue having a contact surface designed to abut against the medical instrument for retaining the medical instrument within the passage.

6. The cassette according to claim 1, wherein the at least one holding means comprises a single spring element.

7. The cassette according to claim 1, wherein the aperture of the at least one holding means is open to a lateral edge of the spring sheet, thereby forming a laterally open passage for allowing insertion of the medical instrument.

8. The cassette according to claim 1, wherein the aperture of the at least one holding means has a closed cross-section such that the medical instrument is inserted into the aperture along an axis coaxial to the passage.

9. The cassette according to claim 1, further comprising a base tray and a cover part forming an outer housing, the at least one spring sheet being located within said outer housing.

10. The cassette according claim 1, further comprising a metal or metal alloy stop sheet, which is provided essentially parallel to and at a distance to the spring sheet.

11. The cassette according to claim 10, wherein:
   the stop sheet is a planar sheet comprising at least one pin, and
   the surface of the stop sheet and the surface of the pin facing the spring sheet form stop surfaces.

12. The cassette according to claim 10, further comprising an intermediate sheet comprising at least one guide hole which is coaxially aligned with the holding means and which is positioned essentially parallel and at a distance to the spring sheet, between the spring sheet and the stop sheet.

13. The cassette according to claim 10, wherein the spring sheet and stop sheet are connected together to form a sandwich unit which can be positioned and removed from the cassette as a single unit.

14. The cassette according to claim 1, wherein the spring sheet comprises a plurality of holding means, each suitable for retaining a medical instrument.

15. The cassette according to claim 1, further comprising one or more secondary holding means comprising a through-hole provided with an undercut, which undercut allows formation of a snap-fit connection to a complementary protrusion provided on the surface of the medical instrument.

16. The cassette according to claim 15, wherein the one or more secondary holding means is formed on the spring sheet, in addition and separately to the at least one holding means, the secondary holding means comprising a cylindrical extension piece having a through-bore comprising the undercut connected to the spring sheet such that it forms an extension of the spring sheet.

17. The cassette according to claim 1, further comprising:
   at least one support sheet comprising at least one aperture shaped to accommodate a medical instrument and open to a lateral side of the support sheet, the support sheet being orientated vertically within the cassette,
   a locking element moveable relative to the at least one support sheet which can be moved from a first position, in which the locking element prevents the medical instrument from being removed from the at least one aperture, to a second position in which the medical instrument can be removed from the at least one aperture, and a retention means comprising an aperture defining a passage therethrough for holding a part of the locking element and a spring element positioned adjacent to the aperture for exerting a biasing spring force to retain the part of the locking element within the passage when the locking element is in the first position, thus preventing movement of the locking element into the second position.

18. The cassette according to claim 1, wherein all components of the cassette are perforated by fluid circulation holes.

19. The cassette according to claim 1, wherein the cassette is comprised entirely of metal or metal alloy.

20. The cassette according to claim 15, wherein the one or more secondary holding means is made of a metal or a metal alloy.

21. A cassette for storage of at least one medical instrument, the cassette comprising:

at least one spring sheet comprising at least one holding means for retaining the medical instrument therein, the holding means comprising:

an aperture forming a passage through the spring sheet for receiving the medical instrument, and at least one spring element provided adjacent to the passage for exerting a biasing spring force to retain the medical instrument within the passage, the at least one spring element comprising a tongue having an attachment end connected to the spring sheet and a free end arranged at the opposing end of the tongue, the tongue having a contact surface designed to abut against the medical instrument for retaining the medical instrument within the passage, wherein the spring sheet, including the holding means, is made of a metal or a metal alloy.

* * * * *